US010697972B2

(12) United States Patent
Short

(10) Patent No.: US 10,697,972 B2
(45) Date of Patent: Jun. 30, 2020

(54) DIAGNOSTICS USING CONDITIONALLY ACTIVE ANTIBODIES

(71) Applicant: BioAtla, LLC, San Diego, CA (US)

(72) Inventor: Jay M. Short, Del Mar, CA (US)

(73) Assignee: BioAtla, LLC, San Diego, CA (US)

( * ) Notice: Subject to any disclaimer, the term of this patent is extended or adjusted under 35 U.S.C. 154(b) by 126 days.

(21) Appl. No.: 15/404,060

(22) Filed: Jan. 11, 2017

(65) Prior Publication Data

US 2017/0199198 A1 Jul. 13, 2017

Related U.S. Application Data

(63) Continuation of application No. PCT/US2017/012830, filed on Jan. 10, 2017.

(60) Provisional application No. 62/277,750, filed on Jan. 12, 2016.

(51) Int. Cl.
*G01N 33/574* (2006.01)

(52) U.S. Cl.
CPC .............................. *G01N 33/57492* (2013.01)

(58) Field of Classification Search
CPC .................................................. G01N 33/574
USPC ........................................................ 435/7.23
See application file for complete search history.

(56) References Cited

U.S. PATENT DOCUMENTS

| | | | |
|---|---|---|---|
| 4,353,888 | A | 10/1982 | Sefton |
| 4,391,909 | A | 7/1983 | Lim |
| 4,689,293 | A | 8/1987 | Goosen et al. |
| 4,803,168 | A | 2/1989 | Jarvis, Jr. |
| 4,806,355 | A | 2/1989 | Goosen et al. |
| 5,227,298 | A | 7/1993 | Weber et al. |
| 5,573,934 | A | 11/1996 | Hubbell et al. |
| 6,790,455 | B2 | 9/2004 | Chu et al. |
| 6,818,230 | B2 | 11/2004 | Asina et al. |
| 7,041,504 | B2 | 5/2006 | Asina et al. |
| 7,297,331 | B2 | 11/2007 | Asina et al. |
| 8,039,218 | B2 | 10/2011 | Hoon |
| 8,202,701 | B2 | 6/2012 | Boyan et al. |
| 8,445,225 | B2 | 5/2013 | Kuhn et al. |
| 2002/0004587 | A1 | 1/2002 | Miller et al. |
| 2002/0098559 | A1 | 7/2002 | Opara |
| 2004/0086493 | A1 | 5/2004 | Hubbell et al. |
| 2004/0170612 | A1 | 9/2004 | Griffith et al. |
| 2005/0037029 | A1 | 2/2005 | Asina et al. |
| 2005/0118425 | A1 | 6/2005 | Childs et al. |
| 2005/0202096 | A1 | 9/2005 | Li et al. |
| 2005/0214377 | A1 | 9/2005 | Mistry et al. |
| 2006/0251630 | A1 | 11/2006 | Stewart et al. |
| 2009/0130718 | A1 | 5/2009 | Short |
| 2009/0214660 | A1 | 8/2009 | Vasconcellos et al. |
| 2009/0269313 | A1 | 10/2009 | Nadler |
| 2011/0064797 | A1 | 3/2011 | Ziouzenkova |
| 2012/0094275 | A1 | 4/2012 | Rao et al. |
| 2012/0164127 | A1 | 6/2012 | Short et al. |
| 2012/0113708 | A1 | 8/2012 | Anderson et al. |
| 2012/0231443 | A1 | 9/2012 | He et al. |
| 2012/0308650 | A1 | 12/2012 | Vegas et al. |
| 2013/0052648 | A1 | 2/2013 | Yarmush et al. |
| 2013/0266579 | A1 | 10/2013 | Wei et al. |
| 2013/0277872 | A1 | 10/2013 | Vincze et al. |
| 2014/0127290 | A1 | 5/2014 | He et al. |
| 2014/0271843 | A1 | 9/2014 | Ma et al. |

FOREIGN PATENT DOCUMENTS

| | | |
|---|---|---|
| WO | WO2010104821 A1 | 9/2010 |
| WO | WO2013134743 A1 | 9/2013 |
| WO | WO2013170168 A1 | 11/2013 |
| WO | WO2014126904 A2 | 8/2014 |
| WO | WO2015092726 A1 | 6/2015 |
| WO | WO2015095603 A1 | 6/2015 |
| WO | WO2015175375 A1 | 11/2015 |
| WO | WO2017078839 A1 | 5/2017 |
| WO | WO2018044619 A1 | 3/2018 |

OTHER PUBLICATIONS

Paoletti et al. (Clin Cancer Res, Nov. 7, 2014, 21(11), 2487-98).*
Vona, Giovanna, et al. "Isolation by size of epithelial tumor cells: a new method for the immunomorphological and molecular characterization of circulating tumor cells." The American journal of pathology 156.1 (2000): 57-63.
Sakadžić, Sava, et al. "Two-photon high-resolution measurement of partial pressure of oxygen in cerebral vasculature and tissue." Nature methods 7.9 (2010): 755-759.
Mayers, Jared R., et al. "Elevation of circulating branched-chain amino acids is an early event in human pancreatic adenocarcinoma development." Nature medicine 20.10 (2014): 1193-1198.
Lorusso, Girieca, and Curzio Rüegg. "The tumor microenvironment and its contribution to tumor evolution toward metastasis." Histochemistry and cell biology 130.6 (2008): 1091-1103.
Gillies, Robert J., et al. "MRI of the tumor microenvironment." Journal of Magnetic Resonance Imaging 16.4 (2002): 430-450.
Hur, Hoon, et al. "Quantitative measurement of organic acids in tissues from gastric cancer patients indicates increased glucose metabolism in gastric cancer." PloS one 9.6 (2014): e98581.
Matsuo, Masayuki, et al. "Magnetic resonance imaging of the tumor microenvironment in radiotherapy: perfusion, hypoxia, and metabolism." Seminars in radiation oncology. vol. 24. No. 3. WB Saunders, 2014.
Butler, Thomas P., and Pietro M. Gullino. "Quantitation of cell shedding into efferent blood of mammary adenocarcinoma." Cancer research 35.3 (1975): 512-516.

(Continued)

*Primary Examiner* — Yan Xiao
(74) *Attorney, Agent, or Firm* — Mendelsohn Dunleavy, P.C.

(57) ABSTRACT

A method of detecting tumor cells in a sample containing cells. In the method, a sample is encapsulated to produce a capsule with the sample encapsulated therein. The capsule containing the sample encapsulated therein is incubated under cell culture conditions suitable for supporting cell activity and growth of tumor cells and the encapsulated sample from the incubated capsule is contacted with a conditionally active antibody that has a higher binding affinity to a cell surface protein of a tumor cell under a first value of a condition of a tumor microenvironment, in comparison with the binding affinity of the conditionally active antibody to the same cell surface protein under a second value of the condition.

18 Claims, 6 Drawing Sheets
(5 of 6 Drawing Sheet(s) Filed in Color)

(56) References Cited

OTHER PUBLICATIONS

Estrella, Veronica, et al. "Acidity generated by the tumor microenvironment drives local invasion." Cancer research 73.5 (2013): 1524-1535.
Dunn-Meynell, Ambrose A., et al. "Relationship among brain and blood glucose levels and spontaneous and glucoprivic feeding." The Journal of Neuroscience 29.21 (2009): 7015-7022.
Benjamin, Scott J., et al. "Measurement of soft tissue temperature and impedance following the application of transdermal direct current." Physiotherapy 93.2 (2007): 114-120.
Swartz, Melody A., et al. "Tumor microenvironment complexity: emerging roles in cancer therapy." Cancer research 72.10 (2012): 2473-2480.
International Search Report and Written Opinion; dated Apr. 18, 2017 for PCT App. No. PCT/US2017/012830.
De Wit, Sanne, et al. "The detection of EpCAM+ and EpCAM— circulating tumor cells." Scientific reports 5 (2015): 12270.
Extended European Search Report for European Patent Application No. 17738795.8; dated Jul. 31, 2019.

* cited by examiner

US 10,697,972 B2

DIAGNOSTICS USING CONDITIONALLY ACTIVE ANTIBODIES

RELATED APPLICATION DATA

This application is a non-provisional of U.S. Provisional Application No. 62/277,750, filed Jan. 12, 2016, the entire disclosure of which is hereby incorporated by reference as if set forth fully herein.

FIELD OF THE DISCLOSURE

This disclosure relates generally to the field of cancer diagnosis by detecting tumor cells in a sample from a subject. Specifically, this disclosure relates to methods of diagnosing cancers by detecting tumor cells in a sample using a conditionally active antibody.

BACKGROUND OF THE DISCLOSURE

Tumors begin shedding tumor cells into the circulation at an early stage of cancer, typically prior to the appearance of clinical symptoms. In general, tumors with a diameter of about 1 mm are vascularized, which leads to as much as 4% of the tumor cells being shed into the circulation in a 24 hour period (Butler & Gullino, *Cancer Res.*, vol. 35, pp. 512-516, 1975). These tumor cells are called circulating tumor cells (CTCs), and are generally, although not exclusively, epithelial cells shed from a solid tumor into the blood stream. CTCs are good indicators of the tumor from which they originated, which may be especially important for diagnosing early stage solid tumors which are usually too small to be detected by conventional methods such as mammography for breast cancer patients, or X-rays for lung cancer patients. Accordingly, detection of CTCs may, in some cases, be used as an early diagnostic tool for cancers, especially early stage cancers before the appearance of clinical symptoms.

However, the CTCs are only a very small fraction of the total cells in circulation. For example, for patients with carcinomas, it is estimated that about only one in ten million cells in the blood is a CTC. In addition, various types of CTCs differ significantly from each other depending on their origins, both in terms of morphology and their inclusion of cancer specific markers. For example, fibroblast-based tumor cells have a different morphology than breast cancer cells which arise from epithelial cells. Also, CTCs originating from breast cancer typically have markers such as CK+/DAPI+/CD45, while CTCs originating from pancreatic cancer typically have markers that include CK8+/CK19+. Therefore, differentiating CTCs originating from different cancers would require using different antibodies to target different markers that are specific for different cancers, optionally in combination with gathering information about cell morphology. These technical complexities make cancer diagnosis by detection of CTCs in a clinical setting very challenging.

An automated system for detecting, enumerating and/or characterizing CTCs in a blood sample employs immunomagnetic enrichment technology to target cancer specific cell surface markers. Another commercial technology for enumerating and/or characterizing CTCs is Fiber-optic Array Scanning Technology (FAST), which investigates nucleated cells from a blood sample as a monolayer of cells on a slide using a fluorescence-labelled antibody against a cancer specific cell surface marker to identify the CTCs on the slide. A third commercial technology is based on the microfluidic or "CTC-Chip" technique. Using breast cancer as an example, 1-3 mL of whole blood is directed to flow past 78,000 EpCam-coated microposts. EpCam+ cells will bind to the microposts and are subsequently stained with antibodies against CK, CD45, and DAPI, which are breast cancer specific cell surface markers.

Besides these commercial methods, other CTC detection methods have been proposed. U.S. Pat. No. 8,445,225 discloses a method for revealing, detecting, and characterizing CTCs in the blood of a patient. The method includes the steps of: a) obtaining a blood sample from a patient; b) removing or degrading a protein, carbohydrate, cell, or a combination thereof, in physical association with the surface of the CTCs present in the sample; and c) analyzing the CTCs revealed in step (b). Step (b) is used for exposing the cell surface of CTCs without causing damage to the CTCs themselves, thereby revealing the CTCs in the sample. The analysis of CTCs in step (c) involves characterizing the morphology of the CTCs via image analysis. The analysis may also include detecting cancer specific cell surface markers on the CTCs, which include EGFR, HER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, and Leukocyte Associated Receptor (LAR).

U.S. Pat. No. 8,039,218 discloses a method of detecting CTCs in a body fluid from a patient. The method comprises obtaining the body fluid from the patient and detecting the expression of a panel of genes in the body fluid, where the expression of the panel of genes indicates the presence of CTCs in the body fluid. Genes useful for detecting melanoma cells includes GalNAc-T, MAGE-A3, MART-1, PAX-3, and TRP-2. Genes useful for detecting carcinoma cells include C-Met, MAGE-A3, Stanniocalcin-1, Stanniocalcin-2, mammaglobin, HSP27, GalNAc-T, CK20, and β-HCG.

WO 2014/126904 discloses a method for detecting CTCs using a labeled pituitary adenylate cyclase activating peptide (PACAP) or vasoactive intestinal peptide (VIP). The PACAP and VIP can both bind to the VPAC1 receptor and detect CTCs present in blood or urine, since the VPAC1 receptor is present on surface of CTCs from many different cancer types. The PACAP has the sequence: His-Ser-Asp-Gly-Ile-Phe-Thr-Asp-Ser-Tyr-Ser-Arg-Tyr-Arg-Lys-Gin-Met-Ala-Val-Lys-Lys-Tyr-Leu-Ala-Ala-Val-Leu-Gly-Lys-Arg-Tyr-Lys-Gln-Arg-Val-Lys-Asn-Lys. The labeled peptide is said to be able to detect CTCs at a concentration of 5 cells/ml sample and correctly identify and distinguish CTCs from epithelial cells and white blood cells contained in the sample.

US 2012/0094275 discloses a highly sensitive assay which combines immunomagnetic enrichment with multiparameter flow cytometry or image cytometry to detect, enumerate and characterize CTCs in a blood sample. The assay uses ferrofluid with different antibodies incorporated therein for detecting CTCs originating from different types of cancer. The multiple antibodies present in the same ferrofluid do not appear to block or otherwise interfere with each other. Such ferrofluids are capable of binding specifically to CTCs of more than one type of cancer. The assay is especially useful to enable the capture of CTCs that have low EpCAM expression, but high expression of other cancer specific markers.

These known methods of detecting CTCs often require use of multiple antibodies to diagnose different types of cancers, without knowing beforehand the cancer type a subject may have. For example, in order to be able to detect a wide range of common cancers, the antibodies will have to include one or more that bind specifically to breast cancer markers consisting of MUC-1, estrogen, progesterone receptor, cathepsin D, p53, urokinase type plasminogen activator, epidermal growth factor, epidermal growth factor receptor, BRCA1, BRCA2, CA27.29, CA15.5, prostate specific antigen, plasminogen activator inhibitor and Her2-neu; one or more that bind specifically to prostate cancer markers consisting of prostate specific antigen, prostatic acid phosphatase, thymosin b-15, p53, HPC1 basic prostate gene, creatine kinase and prostate specific membrane antigen; one or more that bind specifically to colon cancer markers consisting of carcinoembryonic antigen, C protein, APC gene, p53 and matrix metalloproteinase (MMP-9); and one or more that bind specifically to bladder cancer markers consisting of nuclear matrix protein (NMP22), Bard Bladder tumor antigen (BTA), and fibrin degradation product (FDP). Use of such a large number of antibodies significantly increases the cost and rate of false diagnoses when these methods are used in a clinical setting.

The present invention provides a diagnostic method that encapsulates one or more CTCs before detection thereof. Cell encapsulation has been described in, for example, US 2014/0127290 which discloses a method of encapsulating living cells in microcapsules. In the method, the cells are suspended in a matrix within the microcapsules. The microcapsules include a core having living cells or cell aggregates suspended or encapsulated therein and a shell surrounding the core comprising a biocompatible hydrogel. US 2012/0231443 also discloses a method for encapsulating cells in a microcapsule, which has a diameter of less than about 100 µm. The microcapsule may be further coated with chitosan and alginate.

Encapsulation of cells is generally viewed as hindering the detection of the encapsulated cells, since encapsulation introduces an outer layer to the encapsulated cells which may make detection of the cells more difficult. The present invention provides a diagnostic method that involves detection of encapsulated CTCs. The CTCs are encapsulated in manner which renders them more suitable for binding to conditionally active antibodies (CABs).

This technique enables detection of CTCs originating from many different cancer types using a single antibody in a simple procedure. This diagnostic technique is applicable to many different types of cancers and can therefore significantly reduce the cost of screening and diagnosis of early stage cancers while at the same time reducing the number of false positives that result from the use of prior art methods.

SUMMARY OF THE DISCLOSURE

In one aspect, the present invention provides a method of detecting tumor cells in a sample containing cells. The method includes steps of encapsulating the sample to produce a capsule with the sample encapsulated therein; incubating the sample encapsulated in the capsule under cell culture conditions suitable for supporting cell activity and growth of tumor cells; and contacting the encapsulated sample from the incubated capsule with a conditionally active antibody (CAB) that has a higher binding affinity to a cell surface protein of a tumor cell under a first value of a condition of a tumor microenvironment, in comparison with the binding affinity to the same cell surface protein under a second value of the condition. The second value of the condition may be a normal physiological condition.

In another aspect, the capsules of the foregoing method may include a core comprising the cells suspended therein; and a shell comprising a biocompatible polymer. The core may comprise a polymer matrix.

In yet another aspect, the core further of any of the foregoing methods comprises a protein and a nutrient suitable for supporting cell activity and growth of the circulating tumor cells in the core.

In yet another aspect, the CAB of any of the foregoing methods may first be conjugated to a detectable label, which may be a molecule or an ion directly or indirectly detectable based on light absorbance, fluorescence, reflectance, light scatter, phosphorescence, luminescence properties, radioactive properties, nuclear magnetic resonance properties or paramagnetic properties, prior to the contacting step.

In yet another aspect, the cell surface protein of any of the foregoing methods may a protein product of a housekeeping gene, which may be selected from AP2S1, CD81, GPAA1, LGALS9, MGAT2, MGAT4B, VAMP3, SLC2A1, SLC2A2, SLC2A3, SLC2A4, SLC2A5, SLC2A6, SLC2A7, SLC2A8, SLC2A9, SLC2A10, SLC2A11, SLC2A12, SLC2A13, and SLC2A14.

In yet another aspect, the CAB of any of the foregoing methods may have at least a fivefold, or at least a tenfold, or at least a twentyfold or at least a fiftyfold, or at least a seventyfold, or at least a hundredfold, or at least a two hundredfold or at least a five hundredfold or at least a thousand-fold higher binding affinity to the cell surface protein under the first value of the condition than the binding affinity to the same cell surface protein under the second value of the condition.

In yet another aspect, any of the foregoing methods of detecting circulating cells may further comprise a step of expanding a population of the cells in the sample.

In yet another aspect, any of the foregoing methods of detecting circulating cells may further comprise a step of enriching a population of the cells in the sample.

In yet another aspect, any of the foregoing methods of detecting circulating cells may further comprise a step of revealing the tumor cells in the sample.

The present invention also provides a method of detecting tumor cells in a sample containing cells. The method includes steps of:

encapsulating the sample to produce a capsule with the sample encapsulated therein;

incubating the capsule with the encapsulated sample under cell culture conditions suitable for supporting cell activity and growth of tumor cells; and contacting the encapsulated sample of the incubated capsule with a conditionally active antibody that has a higher binding affinity to a cell surface protein on a tumor cell under a first value of a condition of a tumor microenvironment, in comparison with the binding affinity of the conditionally active antibody to the same cell surface protein under a second value of the condition.

In the foregoing embodiment, the capsules may comprise a core comprising the sample with cells suspended therein; and a shell comprising a biocompatible polymer. In each of the foregoing embodiments, the core may comprise a polymer matrix.

In each of the foregoing embodiments, the biocompatible polymer may be selected from proteins and polysaccharides.

In each of the foregoing embodiments, the proteins may be selected from albumin, collagen, synthetic polyamino acids and prolamins.

In each of the foregoing embodiments, the polysaccharides may be selected from alginate, cellulose and heparin.

In each of the foregoing embodiments, the cellulose may be acyl-substituted cellulose.

In each of the foregoing embodiments, the synthetic polymer may be selected from poly(lactide), poly(glycolide), poly(lactide-co-glycolide), poly(caprolactone), polycarbonates, polyamides, polyanhydrides, polyphosphazene, polyamino acids, polyortho esters, polyacetals, polycyanoacrylates, biodegradable polyurethanes, polyacrylates, ethylene-vinyl acetate polymers, acyl-substituted cellulose acetates, polyurethanes, polystyrenes, polyvinyl chloride, polyvinyl fluoride, poly(vinyl imidazole), chlorosulphonated polyolefins, and polyethylene oxide.

In each of the foregoing embodiments, the core may comprise a protein and a nutrient suitable for supporting cell activity and growth of the circulating tumor cells in the core. In the foregoing embodiments, the protein may be selected from collagen, fibrin, gelatin, elastin and elastin-like polypeptide.

In each of the foregoing embodiments, the nutrient may comprise a nutrient osmolyte.

In each of the foregoing embodiments, the capsules may have a diameter from about 10 μm to about 1000 μm, or about 20 μm to about 1000 μm, or about 50 μm to about 1000 μm, or about 50 μm to about 800 μm, or about 100 μm to about 700 μm.

In each of the foregoing embodiments, the incubating step may be carried out for a period of at least about 3 hours.

In each of the foregoing embodiments, the incubating step may be carried out for a period of from about 12 to about 36 hours, or about 18 to about 24 hours.

In each of the foregoing embodiments, the conditionally active antibody may be conjugated to a detectable label. In the foregoing embodiments, the detectable label may be a molecule or an ion directly or indirectly detectable based on light absorbance, fluorescence, reflectance, light scatter, phosphorescence, luminescence properties, radioactive properties, nuclear magnetic resonance properties or paramagnetic properties.

In each of the foregoing embodiments, the detectable label may be a fluorescence label.

In each of the foregoing embodiments, the cell surface protein may be a protein product of a housekeeping gene.

In each of the foregoing embodiments, the housekeeping gene may selected from AP2S1, CD81, GPAA1, LGALS9, MGAT2, MGAT4B, VAMP3, SLC2A1, SLC2A2, SLC2A3, SLC2A4, SLC2A5, SLC2A6, SLC2A7, SLC2A8, SLC2A9, SLC2A10, SLC2A11, SLC2A12, SLC2A13, and SLC2A14.

In each of the foregoing embodiments, the cell surface protein may selected from ABCA7, ABCC1, ABCC5, ABHD3, ACKR3, ADAM10, AQP1, AQP3, ATP13A3, ATP1B3, ATP2B1, ATP2B4, ATP6AP1, ATP6V0A2, BACE1, BMPR2, BNIP2, BST2, BTN2A1, BTN3A3, C12orf76, C17orf62, C1orf27, CCDC107, CD4, CD44, CD46, CD81, CD9, CD99L2, CDAN1, CDIPT, CLCN6, CNNM4, CYP20A1, DCBLD2, DHRS7B, ERBB2, ETNK1, FAM210B, GINM1, GPI, GRAMD1A, HELZ, HERPUD1, HMOX1, HPS3, ICAM1, IFI30, IFRD1, IL15RA, IL6ST, ITGA7, ITGB1, ITGB4, ITGB5, ITSN1, JAG1, LAIR1, LMTK2, LRBA, LRP12, LSR, MACF1, MADD, MCAM, MCOLN1, MET, MICAL3, MPV17L2, NCKIPSD, NDC1, NEO1, NOTCH2, PANX1, PDLIM5, PFDN1, PGAP3, PGRMC2, PHLDB2, PIGN, PIGQ, PIGW, PKN2, PTPRS, PVR, RALGAPA2, RNF145, RNF149, SC5D, SCAMP4, SDC2, SDC4, SLC12A2, SLC16A1, SLC16A3, SLC17A5, SLC19A1, SLC1A5, SLC30A1, SLC38A6, SLC38A7, SLC39A14, SLC3A2, SLC43A1, SLC46A1, SLC46A3, SLC4A2, SLC4A7, SLC7A5, SLC9A1, SMAGP, SORT1, SPG11, SPINT2, SPPL2B, SPPL3, SRD5A3, SRPRB, STX18, STX4, SYVN1, TAPT1, TAZ, TBC1D5, TGFBR2, TM2D2, TMEM183A, TMEM205, TMEM218, TMEM222, TMEM245, TMEM258, TMEM50A, TMEM63B, TMEM97, TNFRSF12A, TXNDC11, UBR2, UQCC1, VSIG4, WWP1, YIPF4, ZDHHC20 and ZDHHC5.

In each of the foregoing embodiments, the first value of the condition may be a pH in a range of 6.0-6.8 and the second value of the condition may be a pH in a range of 7.0-7.8.

In each of the foregoing embodiments, the first value of the condition may be a pH in a range of 6.2-6.8 and the second value of the condition may be a pH in a range of 7.2-7.6.

In each of the foregoing embodiments, the first value of the condition may be a partial oxygen pressure in a range of from about 1 to about 20 mmHg and the second value of the condition may be a partial oxygen pressure in a range of from about 30 to about 50 mmHg.

In each of the foregoing embodiments, the first value of the condition may be a partial oxygen pressure in a range of from about 5 to about 10 mmHg and the second value of the condition may be a partial oxygen pressure in a range of from about 30 to about 50 mmHg.

In each of the foregoing embodiments, the first value of the condition may be a glucose concentration in a range of from about 0.05 to about 0.5 mM and the second value of the condition may be a glucose concentration in a range of from about 2.5 to about 10 mM.

In each of the foregoing embodiments, the conditionally active antibody may have a binding affinity to the cell surface protein under the first value of the condition higher than a binding affinity to the same cell surface protein under the second value of the condition by at least about 5 fold, or at least about 10 fold, or at least about 20 fold, or at least about 50 fold, or at least about 70 fold, or at least about 100 fold, or at least about 200 fold, or at least about 500 fold, or at least about 700 fold, or at least about 1000 fold.

In each of the foregoing embodiments, the conditionally active antibody may be a multi-specific antibody.

In each of the foregoing embodiments, the method may further comprise a step of expanding a population of the cells in the sample. In the foregoing embodiments, the step of expanding the population of cells may comprise culturing the cells in the sample under a cell culture condition suitable for growth of tumor cells. In the foregoing embodiments, the culturing may be carried out for a period of from about 3 to about 21 days, or from about 5 to about 18 days, or from about 7 to about 15 days.

In each of the foregoing embodiments, the method may further comprise a step of enriching a population of the cells in the sample. In the foregoing embodiments, the enriching step may comprise using a technique selected from fractionation, red blood cell lysis, cell sorting, filtration, adhesion, density centrifugation, and ammonium chloride lysis.

In each of the foregoing embodiments, the method may further comprise a step of revealing tumor cells in the sample. In the foregoing embodiments, the revealing step may comprise using a technique selected from enzymatic treatment, mechanic treatment, electric treatment, electromagnetic treatment, chemical treatment, and combinations thereof.

In each of the foregoing embodiments, the second value of the condition is a normal physiological condition.

In each of the foregoing embodiments, the method may further comprise the step of determining a presence of a tumor cell in the sample based on binding of said conditionally active antibody in said contacting step.

BRIEF DESCRIPTION OF THE DRAWINGS

The application file contains at least one drawing executed in color. Copies of this patent application publication with color drawings will be provided by the Office upon request and payment of the necessary fee.

DEFINITIONS

Figure 1:
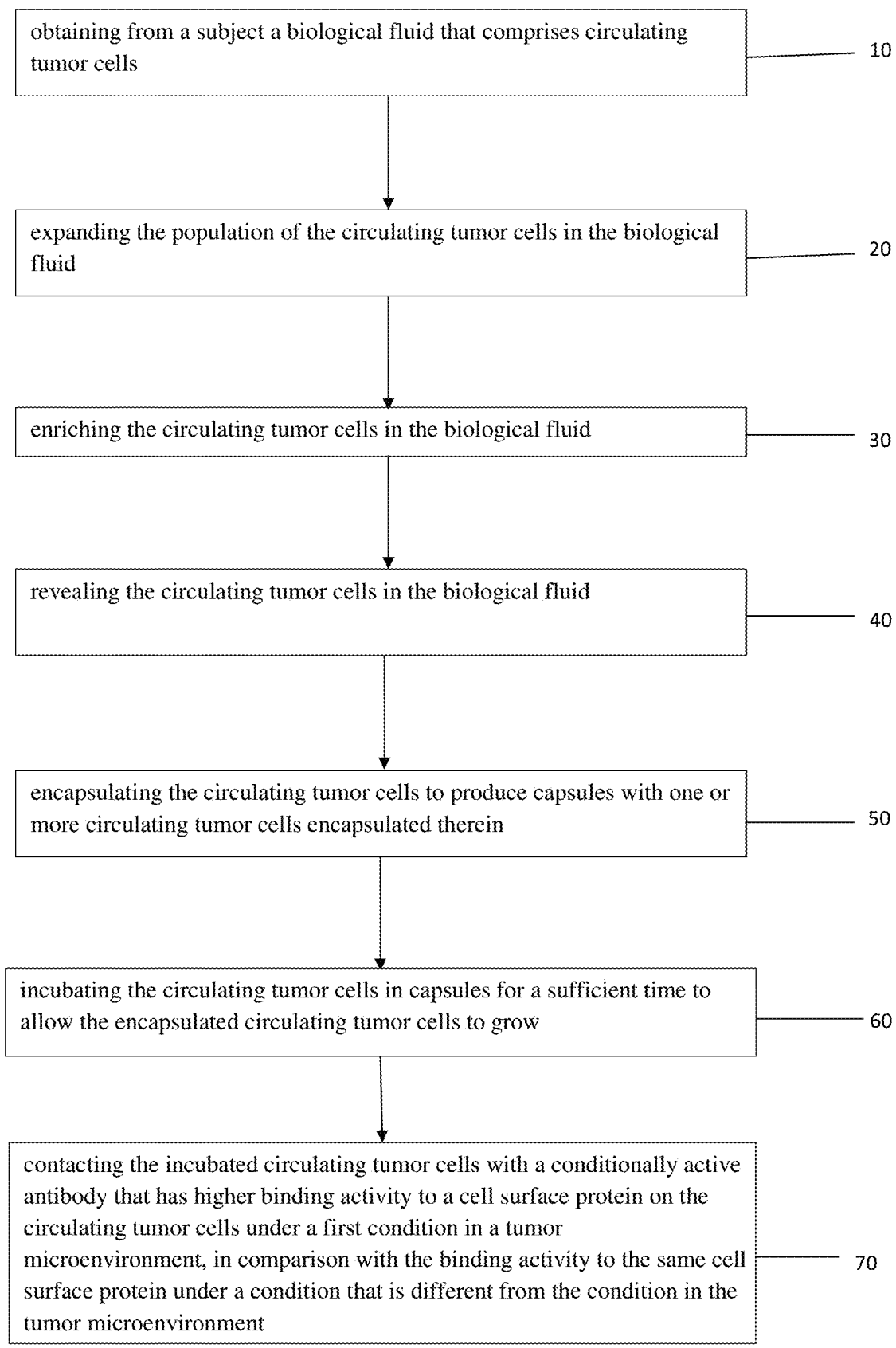
FIG. 1 is a flow chart representing a method for detecting CTCs in a sample according to one embodiment of the present invention.

In order to facilitate understanding of the examples provided herein, certain frequently occurring terms are defined herein.

In connection with a measured quantity, the term "about" as used herein refers to the normal variation in that measured quantity that would be expected by a skilled person making the measurement and exercising a level of care commensurate with the objective of the measurement and the precision of the measuring equipment used. Unless otherwise indicated, "about" refers to a variation of +/−10% of the value provided.

The term "biocompatible" as used herein refers to a material and any metabolites or degradation products thereof that are generally non-toxic to the recipient of the material and do not cause any significant adverse effects to the recipient.

The term "binding" as used herein refers to interaction of the variable region or an Fv of an antibody with an antigen with the interaction depending upon the presence of a particular structure (e.g., an antigenic determinant or epitope) on the antigen. For example, an antibody variable region or Fv recognizes and binds to a specific protein structure rather than to proteins generally.

As used herein, the term "specifically binding" or "binding specifically" means that an antibody variable region or Fv binds to or associates with more frequently, more rapidly, with greater duration and/or with greater affinity with a particular antigen than with other proteins. For example, an antibody variable region or Fv specifically binds to its antigen with greater affinity, avidity, more readily, and/or with greater duration than it binds to other antigens. For another example, an antibody variable region or Fv binds to a cell surface protein (antigen) with materially greater affinity than it does to related proteins or other cell surface proteins or to antigens commonly recognized by polyreactive natural antibodies (i.e., by naturally occurring antibodies known to bind a variety of antigens naturally found in humans). However, "specifically binding" does not necessarily require exclusive binding or non-detectable binding of another antigen, this is meant by the term "selective binding". In one example, "specific binding" of an antibody variable region or Fv (or other binding region) binds to an antigen, means that the an antibody variable region or Fv binds to the antigen with an equilibrium constant (KD) of 100 nM or less, such as 50 nM or less, for example 20 nM or less, such as, 15 nM or less, or 10 nM or less, or 5 nM or less, 2 nM or less, or 1 nM or less.

The term "sample" as used herein means a sample obtained from a subject, typically a subject having cancer, suspected of having cancer, (e.g., exhibiting one or more symptoms associated with cancer), a subject at risk of having cancer (e.g., because of predisposition or exposure to a carcinogen), a subject who has been treated for cancer or a subject being screened for cancer. Desirably, the sample is obtained from a mammal, such as a canine, feline, rodent (e.g., mouse and rat), bovine, ovine, or and primate (e.g., human). In a particular embodiment, the sample is obtained from a human. In a preferred embodiment, the sample is a bodily fluid, including one or more components in or obtained from blood, lymph, saliva, mucus, sputum, pus, urine, stool, gastro-intestinal secretions, cochlear fluid, synovial fluid, cerebrospinal fluid, lachrymal fluid, vitreous humor, semen, vaginal secretions, and mammary gland secretions. In particular embodiments, the sample is blood, urine or cerebrospinal fluid.

The term "cell surface protein" as used herein means a protein that is displayed on the surface of a cell such that it is capable of being bound by another molecule, such as an antibody. The cell surface protein may be physically embedded in the lipid membrane of a cell, or just bound or aggregated to the surface of the cell. In some embodiments, the cell surface protein can be post-translationally modified (e.g., can be a glycoprotein or a phosphoprotein) and the antibody can bind to the modification. In some embodiments, the cell surface protein can be part of a complex and the antibody can bind to the protein as part of the complex or to the complex. For example, cell surface proteins may include, but are not limited to surface antigens, transmembrane receptors or co-receptors, macromolecules bound to the surface, such as bound or aggregated proteins or carbohydrates, internal cellular components, and the like.

The term "circulating tumor cell" (CTC) as used herein refers to a tumor cell released or shed from a primary tumor and transported/released into the circulatory system (e.g., blood and lymph). The circulating tumor cell may enter a tissue or organ that is different from the location of the tumor from which the CTC was shed from and become secondary tumors or metastatic tumors. Further, blood cancer cells such as are found in the blood in subjects with leukemia, lymphoma and myeloma are considered circulating tumor cells for the purpose of this invention.

The term "tumor" as used herein refers to any neoplastic cell growth and proliferation that forms an abnormal mass of tumor cells. The tumor may be malignant or benign, including all pre-cancerous and cancerous cells and tissues. Many types of tumors are known to metastasize and shed circulating tumor cells or be metastatic, for example, a secondary tumor resulting from a primary tumor that has metastasized. Tumors may occur in the following organs or systems: brain, cardiac, lung, gastrointestinal, genitourinary tract, liver, bone, nervous system, gynecological, hematologic, skin, breast, and adrenal glands. Non limiting types of Tumors include gliomas (Schwannoma, glioblastoma, astrocytoma), neuroblastoma, pheochromocytoma, paraganlioma, meningioma, adrenalcortical carcinoma, medulloblastoma, rhabdomyoscarcoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia, and skin cancers including malignant melanoma, basal cell carcinoma, squamous cell carcinoma, Karposi's sarcoma, moles dysplastic nevi, lipoma, angioma, dermatofibroma, keloids, sarcomas such as fibrosarcoma or hemangiosarcoma, and melanoma.

The term "condition" as used herein refers to any condition that may be encountered in a microenvironment of the subject including at least temperature, pH, concentration of small organic molecules such as glucose, lactic acid, pyruvate, nutrient components, other metabolites, and the like, concentration of molecules such as oxygen, carbon dioxide, and electrolytes, as well as cell types, nutrient availability, and osmotic pressure.

The term "conditionally active antibody" or "CAB" as used herein refers to a variant, or mutant, wild-type antibody which is more or less active compared to parent wild-type antibody from which the CAB was derived, under one or more conditions. This CAB may also exhibit activity in one or more selected regions of the body and/or exhibit increased or decreased activity under aberrant, or permissive, physiological conditions. Normal physiological conditions are those of temperature, pH, concentration of small organic molecules such as glucose, lactic acid, pyruvate, nutrient components, other metabolites, and the like, concentration of molecules such as oxygen, carbon dioxide, and electrolytes, as well as cell types, nutrient availability, osmotic pressure which would be considered within a normal range in the sample described herein wherein the sample is a sample substantially free from CTCs or sample with capsules free of CTCs. An aberrant condition is that which deviates from the normally acceptable range for that condition at that location in that subject. For example, the conditions encountered in normal blood are considered to be normal physiological conditions whereas one or more conditions encountered in a tumor microenvironment may be considered aberrant conditions if they vary from the normal condition at that location in that subject. In one aspect, the CAB is virtually inactive at one or more normal physiological conditions but is active under one or more aberrant conditions such as under an aberrant condition in a tumor microenvironment. For example, a CAB may be virtually inactive at a normal body temperature of the subject, but may be active at a higher temperature such as may be encountered in a tumor microenvironment of that subject.

In another aspect, the CAB may be reversibly or irreversibly inactivated under normal physiological conditions. In yet another aspect, the CAB is inactive or has a low activity in normal oxygenated blood, and is more active in a less oxygenated environment such as may be present in a tumor. In yet another aspect, the CAB is inactive or has a low activity at a normal physiological pH of, for example, from 7.2 to 7.8, and is more active at an acidic pH of, for example, from 6.0 to 7.0, or from 6.2 to 6.8 that may be encountered in a tumor microenvironment.

The term "detectable label" as used herein refers to any substance whose detection or measurement, either directly or indirectly, by physical or chemical means, is indicative of the presence of one or more CTCs in a sample. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules.

The term "diagnostics" as used herein refers to a determination of a subject's susceptibility to a disease or disorder, a determination as to whether a subject is presently affected by a disease or disorder, prognosis of a subject affected by a disease or disorder (e. g., identification of pre-metastatic or metastatic cancerous states, stages of cancer, or responsiveness of cancer to therapy), and therametrics (e. g., monitoring a subject's condition to provide information as to the effect or efficacy of therapy). In some embodiments, the diagnostic methods of this invention are particularly useful in detecting early stage cancer.

The term "early stage cancer" as used herein refers to a cancer, which is in such an early stage of development that it cannot be detected by conventional cancer screening methods. One example of an early stage cancer is a tumor that is too small to be detected by conventional methods such as mammography for breast cancer patients, or X-rays for lung cancer patients. Early stage cancer includes any pre-cancerous state or early cancer state that may occur prior to late stage cancer, including but not limited to benign conditions, conditions prior to invasive carcinoma, and/or conditions prior to the development of a cancerous tumor. Late stage cancer is cancer that is detectable using conventional cancer screening methods. With regard to breast cancer, "early stage cancer" includes any pre-cancerous state prior to stage I, stage II, stage III, or stage IV cancer, as described in more detail below. Examples of early stage breast cancer include benign conditions (e.g., non-proliferative lesions, proliferative lesions without atypia, and proliferative lesions with atypia), dysplasia, and/or carcinoma in situ. With regard to cancers other than breast cancer (e.g., glioma, bladder cancer, colon cancer, esophagus cancer, hepatocellular carcinoma, larynx cancer, lung cancer, skin cancer, ovarian cancer, prostate cancer, pancreatic cancer, renal cancer, or stomach cancer), "early stage cancer" includes any pre-cancerous state prior to late stage cancer, such as those that correspond to stage I, stage II, stage III, or stage IV in breast cancer.

As used herein, the term "electrolyte" is used to define a mineral in the blood or other body fluids that carries a charge. For example, in one aspect, the normal physiological condition and aberrant condition can be conditions of "electrolyte concentration". In one aspect, the electrolyte concentration to be tested is selected from one or more of ionized calcium, sodium, potassium, magnesium, chloride, bicarbonate, and phosphate concentration. For example, in one aspect, normal range (i.e., normal physiological condition) of serum calcium is 8.5 to 10.2 mg/dL. In this aspect, aberrant serum calcium concentration may be selected from either above or below the normal range, in another example, in one aspect, normal range (i.e., normal physiological condition) of serum chloride is 96-106 milliequivalents per liter (mEq/L). In this aspect, aberrant serum chloride concentration may be selected from either above or below the normal range, in another example, in one aspect, a normal range (i.e., normal physiological condition) of serum magnesium is from 1.7-2.2 mg/dL. In this aspect, an aberrant serum magnesium concentration may be selected from either above or below the normal range, in another example, in one aspect, a normal range of serum phosphorus is from 2.4 to 4.1 mg/dL. In this aspect, aberrant serum phosphorus concentration may be selected from either above or below the normal range. In another example, in one aspect, a normal range of serum, or blood, sodium is from 135 to 145 mEq/L.

In this aspect, aberrant serum, or blood, sodium concentration may be selected from either above or below the normal range. In another example, in one aspect, a normal range of serum, or blood, potassium is from 3.7 to 5.2 mEq/L. In this aspect, aberrant serum, or blood, potassium concentration maybe selected from either above or below the normal range. In a further aspect, a normal range of serum bicarbonate is from 20 to 29 mEq/L. In this aspect, aberrant serum, or blood, bicarbonate concentration may be selected from either above or below the normal range. In a different aspect, bicarbonate levels can be used to indicate normal levels of acidity (pH), in the blood. The term "electrolyte concentration" may also be used to define the condition of a particular electrolyte in a tissue or body fluid other than blood or plasma. In this case, the normal physiological condition is considered to be the clinically normal range for that tissue or fluid. In this aspect, aberrant tissue or fluid electrolyte concentration may be selected from either above or below the normal range, such as in a tumor microenvironment.

The term "epitope" as used herein refers to an antigenic determinant on an antigen, such as an enzyme polypeptide, to which the paratope of an antibody, such as an enzyme-specific antibody, binds. Antigenic determinants usually consist of chemically active surface groupings of molecules, such as amino acids or sugar side chains, and can have specific three-dimensional structural characteristics, as well as specific charge characteristics. Thus, an epitope is a portion of an antigen or other macromolecule capable of forming a binding interaction that interacts with the variable region of an antibody. Typically, such binding interaction is manifested as an intermolecular contact with one or more amino acid residues of a CDR in the variable region.

The term "evolution", or "evolving" as used herein refers to using one or more methods of mutagenesis to generate a novel polynucleotide encoding a novel polypeptide, which novel polypeptide is itself an improved biological molecule and/or contributes to the generation of another improved biological molecule. In a particular non-limiting aspect, the present disclosure relates to evolution of conditionally active biologic proteins from a parent wild type protein. In one aspect, for example, evolution relates to a method of performing both non-stochastic polynucleotide chimerization and non-stochastic site-directed point mutagenesis disclosed in U.S. patent application publication 2009/0130718, which is incorporated herein by reference. More particularly, the present disclosure provides methods for evolution of conditionally active biologic enzymes which exhibit reduced activity at normal physiological conditions compared to a wild-type enzyme parent molecule, but enhanced activity under one or more aberrant conditions compared to the wild-type enzyme.

The term "fluorescent label" as used herein refers to a fluorophore that can be covalently attached to another molecule, such as a CAB, which attachment is generally accomplished by using a reactive derivative of the fluorophore that selectively binds to a functional group contained in the target molecule. Fluorescent labels include, but are not limited to fluoresceins (fluoresceins, FITC), rhodamines (FAM, R6G, TET, TAMRA, JOE, HEX, CAL Red, VIC, and ROX), Texas red, BODIPY, coumarins, cyanine dyes (thiazole orange [TO], oxazole yellow [YO], TOTO, YOYO; Cy3, Cy5), Alexa dyes, green fluorescen protein (GFP) and phycoerythrin (PE).

The term "full length antibody" refers to an antibody which comprises an antigen-binding variable region ($V_H$ or $V_L$) as well as a light chain constant domain (CL) and heavy chain constant domains, CH1, CH2 and CH3. The constant domains may be native sequence constant domains (e.g. human native sequence constant domains) or amino acid sequence variants thereof. Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known.

The term "hydrogel" as used herein refers to a substance formed when an organic polymer (natural or synthetic) is cross-linked via covalent, ionic, or hydrogen bonds to create a three-dimensional open-lattice structure which entraps water molecules to form a gel. Biocompatible hydrogel refers to a polymer that forms a gel which is not toxic to living cells entrapped within, and allows sufficient diffusion of oxygen and nutrients to the entrapped cells to maintain viability.

The term "microcapsule" as used herein refers to a capsule having a mean diameter of about 10 µm to about 1000 µm, or about 20 µm to about 1000 µm, or about 50 µm to about 1000 µm, or about 50 µm to about 800 µm, or about 100 µm to about 700 µm, with a shell surrounding a liquid or a biocompatible matrix. The microcapsule may contain one or more CTCs dispersed in the liquid or biocompatible matrix, thereby "encapsulating" the CTCs. In some embodiments, the CTCs may be encapsulated in capsules that are larger than microcapsules, up to 2000 µm, or 3000 µm. The microcapsule and larger capsule are generally referred to as "capsules" in this application. The CTCs are suspended in the liquid or matrix within the capsules. For example, the matrix can be a viscous aqueous liquid or a hydrogel. In some embodiments, the liquid or hydrogel contains proteins suitable for promoting a cell activity, such as survival, attachment, or growth. For example, the protein can be collagen, fibrin, gelatin, elastin, or elastin-like polypeptides (ELPs), or a derivative thereof. In addition, the liquid or matrix may also contain various nutrients necessary for the CTCs' survival and growth.

The term "microenvironment" as used herein means any portion or region of a tissue or body that has at least one constant or temporal, physical or chemical difference from other regions of the tissue or regions of the body. For tumors, the term "tumor microenvironment" as used herein refers to the environment in which a tumor exists, which is the non-cellular area within the tumor and the area directly outside the tumorous tissue but does not pertain to the intracellular compartment of the cancer cell itself. The tumor and the tumor microenvironment are closely related and interact constantly. A tumor can change its microenvironment, and the microenvironment can affect how a tumor grows and spreads. Typically, the tumor microenvironment has a low pH in the range of 6.0 to 7.0, more commonly in the range of 6.2 to 6.8, most commonly in the range of 6.4-6.8. The tumor microenvironment is also known to have lower concentration of glucose and other nutrients, and a higher concentration of lactic acid, in comparison with blood plasma. Further, the tumor microenvironment can have a temperature that is 0.3 to 1° C. higher than the normal physiological temperature. The tumor microenvironment has been discussed in, among other publications, Gillies et al., "MRI of the Tumor Microenvironment," *Journal of*

*Magnetic Resonance Imaging*, vol. 16, pp. 430-450, 2002, "Tumor microenvironment," edited by Dietmar W. Siemann, Wiley-Blacwell, 2010, and "The tumor microenvironment," edited by Rebecca G. Bagley, Springer, 2010, Swarts et al. "Tumor Microenvironment Complexity: Emerging Roles in Cancer Therapy," *Cancer Res*, vol., 72, pp. 2473-2480, 2012, and Estrella et al., "Acidity Generated by the Tumor Microenvironment Drives Local Invasion," *Cancer Res.*, vol. 73, pages 1524-1535, 2013; Lorusso et al., "The tumor microenvironment and its contribution to tumor evolution toward metastasis," *Histochem Cell Biol*, vol. 130, pages 1091-1103, 2008, hereby incorporated by reference herein its entirety. The term "non-tumor microenvironment" refers to a microenvironment that is not proximate to a tumor.

The term "multispecific antibody" as used herein is an antibody having binding specificities for at least two different epitopes. Exemplary multispecific antibodies may bind to both a BBB-R and a brain antigen. Multi-specific antibodies can be prepared as full-length antibodies or antibody fragments (e.g. $F(ab')_2$ bispecific antibodies). Engineered antibodies with two, three or more (e.g. four) functional antigen binding sites are also contemplated (see, e.g., US 2002/0004587 A1).

The term "mutations" as used herein means changes in the sequence of a wild-type nucleic acid or changes in the sequence of a wild-type peptide. Such mutations may be point mutations such as transitions or transversions. The mutations may be deletions, insertions or duplications.

The term "naturally-occurring" as used herein and as applied to a molecule refers to the fact that the molecule can be found in nature. For example, a polypeptide or polynucleotide sequence that is present in an organism (including viruses) that can be isolated from a source in nature and which has not been intentionally modified by man in the laboratory is naturally occurring. Generally, the term "naturally occurring" refers to a molecule as present in a non-pathological (un-diseased) individual, such as would be typical for the species. Regarding amino acids, the naturally occurring amino acids include the 20 amino acids typically found in a natural protein.

The term "normal physiological conditions", or "wild type operating conditions", as used here are those conditions of temperature, pH, osmotic pressure, osmolality, oxygen partial pressure and electrolyte concentration which would be considered within a normal range of the sample substantially free of CTCs or sample with capsules free of CTCs. The normal physiological conditions include normal physiological temperature at 37-37.5° C., normal physiological pH 7.2-7.8 and normal concentrations of oxygen, lactic acid and glucose in blood plasma, which may be readily determined by a person skilled in the art. In some embodiments, the conditions include temperature, pH, concentration of small organic molecules such as glucose, lactic acid, pyruvate, nutrient components, other metabolites, and the like, concentration of molecules such as oxygen, carbon dioxide, and electrolytes, as well as cell types, nutrient availability, and osmotic pressure.

The terms "revealing" and "revealing for" as used herein generally pertain to altering a CTC in its natural state so as to make the CTC more amenable to detection, analysis, characterization, and/or further processing. One method for revealing a CTC is enrichment. Revealing a CTC may include removing and/or degrading, all or some biomolecules aggregated and/or associated with the surface and/or surface components of the CTC. For example, revealing a CTC may include unmasking or unveiling the CTC by removing, degrading, or altering cells (e.g., platelets), carbohydrates, and/or proteins (e.g., fibrin) aggregated and/or physically associated with the surface of the CTC allowing access to one or more CTC cellular components, such as surface components, including for example, cancer surface markers and other surface bound cellular components, as well as intracellular components, such as nucleic acids and other intracellular components (e.g., nuclear and cytosolic proteins, and the like). As such, "unmasking" and/or "unveiling" are intended to include altering a feature of a CTC in its natural state that may assist in cloaking the CTC from immune recognition or response by the host and/or making the CTC more amenable to detection, analysis, characterization, and/or further processing. Revealing a CTC may also include altering a CTC cellular component, such as an epitope of a cell surface marker, or protein physically associated and/or aggregated with the CTC.

The term "patient", "individual" or "subject", refers to an animal, for example a mammal, such as a human, who is the object of treatment. The subject, or patient, may be either male or female. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "physiological conditions" as used herein refers to temperature, pH, osmotic pressure, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Normal physiological conditions refer to conditions of temperature, pH, concentration of small organic molecules such as glucose, lactic acid, pyruvate, nutrient components, other metabolites, and the like, concentration of molecules such as oxygen, carbon dioxide, and electrolytes, as well as cell types, nutrient availability, and osmotic pressure in the sample substantially free of CTCs or in capsules free of CTCs, which would be considered within the normal range in a patient.

The term "polyepitopic specificity" as used herein refers to the ability of a multispecific antibody to specifically bind to two or more different epitopes on the same target or on different targets.

The term "recombinant antibody", as used herein, refers to an antibody (e.g. a chimeric, humanized, or human antibody or antigen-binding fragment thereof) that is expressed by a recombinant host cell comprising nucleic acid encoding the antibody. Examples of "host cells" for producing recombinant antibodies include: (1) mammalian cells, for example, Chinese Hamster Ovary (CHO), COS, myeloma cells (including Y0 and NS0 cells), baby hamster kidney (BHK), Hela and Vero cells; (2) insect cells, for example, sf9, sf21 and Tn5; (3) plant cells, for example plants belonging to the genus *Nicotiana* (e.g. *Nicotiana tabacum*); (4) yeast cells, for example, those belonging to the genus *Saccharomyces* (e.g. *Saccharomyces cerevisiae*) or the genus *Aspergillus* (e.g. *Aspergillus niger*); (5) bacterial cells, for example *Escherichia. coli* cells or *Bacillus subtilis* cells, etc.

The term "diagnostic agent" as used herein refers to a molecule which can be directly or indirectly detected and is used for diagnostic purposes. The diagnostic agent may be administered to a subject or a sample. The diagnostic agent can be provided per se or may be conjugated to a vehicle such as a CAB.

The term "treating" as used herein includes: (1) preventing or delaying the appearance of clinical symptoms of the state, disorder or condition developing in an animal that may be afflicted with or predisposed to the state, disorder or condition but does not yet experience or display clinical or subclinical symptoms of the state, disorder or condition; (2) inhibiting the state, disorder or condition (i.e., arresting, reducing or delaying the development of the disease, or a relapse thereof in case of maintenance treatment, of at least one clinical or subclinical symptom thereof); and/or (3) relieving the condition (i.e., causing regression of the state, disorder or condition or at least one of its clinical or subclinical symptoms). The benefit to a patient to be treated is either statistically significant or at least perceptible to the patient or to the physician.

The term "variant" as used herein refers to polynucleotides or polypeptides of the disclosure modified at one or more base pairs, codons, introns, exons, or amino acid residues (respectively) of a wild-type protein parent molecule. Variants can be produced by any number of means including methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, saturation mutagenesis and any combination thereof. Techniques for producing variant proteins having reduced activity compared to the wild-type protein at a normal physiological condition of e.g., one or more conditions of temperature, pH, osmotic pressure, osmolality, oxidation and electrolyte concentration; and enhanced activity at an aberrant condition, are disclosed herein. Variants may additionally be selected for the properties of enhanced chemical resistance, and proteolytic resistance, compared to the wild-type protein.

As used herein, the term "wild-type" means that the polynucleotide does not comprise any mutations. A "wild type protein", "wild-type protein", "wild-type biologic protein", or "wild type biologic protein", refers to a protein which can be isolated from nature that will be active at a level of activity found in nature and will comprise the amino acid sequence found in nature. The terms "parent molecule" and "target protein" also refer to the wild-type protein.

DETAILED DESCRIPTION

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in, other systems and methods. Before explaining the disclosed embodiments of the present invention in detail, it is to be understood that the invention is not limited in its application to the details of any particular embodiment shown. Additionally, the terminology used herein is for the purpose of description and not for limitation. Furthermore, although certain methods are described with reference to steps that are presented herein in a certain order, in many instances, these steps can be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more", and "at least one" can be used interchangeably herein. The terms "comprising", "including", "having" and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent, or parameter disclosed herein is to be interpreted as being disclosed for use alone or in combination with one or more of each and every other component, compound, substituent, or parameter disclosed herein.

It is also to be understood that each amount/value or range of amounts/values for each component, compound, substituent, or parameter disclosed herein is to be interpreted as also being disclosed in combination with each amount/value or range of amounts/values disclosed for any other component(s), compounds(s), substituent(s), or parameter(s) disclosed herein and that any combination of amounts/values or ranges of amounts/values for two or more component(s), compounds(s), substituent(s), or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, substituent, or parameter disclosed in the description or an example is to be interpreted as a disclosure of either a lower or an upper limit of a range and thus can be combined with any other lower or upper limit of a range or specific amount/value for the same component, compound, substituent, or parameter disclosed elsewhere in the application to form a range for that component, compound, substituent, or parameter.

The present disclosure is directed to a method for detecting tumor cells and especially circulating tumor cells (CTCs) in a sample using a CAB (FIG. 1). In one embodiment, the diagnostic method includes steps of encapsulating 50 the CTCs in capsules, incubating 60 the CTCs in the capsules for a sufficient time such that the encapsulated CTCs can live and grow thereby altering the environment in the capsules, and contacting 70 the incubated CTCs with the CAB.

The CAB used herein may be a complete antibody or an antibody fragment that can specifically bind to a cell surface protein on the tumor cells and/or CTCs. The CAB is more active in binding to the cell surface protein under a first value of a condition of a tumor microenvironment but less active in binding to the same cell surface protein under a second value of the condition that is different from the first value of the condition. The condition is always the same condition and may be selected from, for example, temperature, pH, concentration of small organic molecules such as glucose, lactic acid, pyruvate, nutrient components, other metabolites, and the like, concentration of molecules such as oxygen, carbon dioxide, and electrolytes, as well as cell types, nutrient availability, and osmotic pressure.

For example, in one embodiment, the CAB may be more active at a first pH that is typical of the tumor microenvironment, e.g., a pH of 6.0-7 or a pH of 6.2-6.8, in comparison with a second pH, e.g., pH 5-6 or pH 7-7.8 (normal physiological pH). In another embodiment, the condition may be an oxygen level (partial oxygen pressure) in a fluid, such that the CAB is more active at a first oxygen level that is typical of a tumor microenvironment, e.g., a partial oxygen pressure of about 1-20 mmHg, or about 5-10 mmHg, in comparison with the activity at a second oxygen level that is typical of a normal physiological condition, e.g., a partial oxygen pressure of about 30-50 mmHg that may be present in blood plasma located in veins.

The conditionally active antibodies useful in the present invention can be generated by any suitable method. In some embodiments, the CAB may be produced using the method described in US 2012/0164127 A1, which is hereby incorporated by reference herein in its entirety. The CAB may also be generated or selected by any other known method that can be used to evolve and/or select an antibody that is more active under one condition than under another condition. For example, the CAB may be selected by screening a library, preferably a mutant antibody library, for an antibody with higher binding affinity to a particular cell surface protein under a first value of the condition than the binding affinity to the same cell surface protein under the second value of the condition.

The first value of the condition is used in the present invention to trigger the conditional activity of the CAB. The first value of the condition is preferably an aberrant condition that differs from a second value of the same condition found elsewhere in the subject such as a normal physiological condition. In one embodiment, the first value of the condition is found in a tumor microenvironment and differs from a normal physiological condition of the subject. The condition may be any condition found in the cancer or tumor microenvironment, including, for example, temperature, pH, concentration of small organic molecules such as glucose, lactic acid, pyruvate, nutrient components, other metabolites, and the like, concentration of molecules such as oxygen, carbon dioxide, and electrolytes, as well as cell types, nutrient availability, and osmotic pressure, or any other condition that differs from a normal physiological condition.

The second value of the condition is a different value of the same condition, e.g. temperature, pH, concentration of small organic molecules such as glucose, lactic acid, pyruvate, nutrient components, other metabolites, and the like, concentration of molecules such as oxygen, carbon dioxide, and electrolytes, as well as cell types, nutrient availability, and osmotic pressure, except that it has a value that is numerically different from the first value of the condition. Thus, the second value of the condition may be a different pH than the first pH value of the condition. The second value of the condition may be a different oxygen partial pressure than the first value of the oxygen partial pressure. The second value of the condition is not required to be, but is preferably a normal physiological condition, such as a normal physiological pH of 7.2-7.8, a normal physiological temperature of 37-37.5° C., or a normal physiological oxygen partial pressure.

The CABs used herein can be triggered in one of two ways. In one aspect, the first value of the condition may be a value that promotes the desired activity of the CAB relative to the second value of the condition such that the desired activity of the CAB is higher at the first value of the condition than at the second value of the condition. In another aspect, the second value of the condition may be a value of the condition that inhibits the desired activity of the CAB relative to the first value of the condition such that again the desired activity of the CAB is higher at the first value of the condition than at the second value of the condition due to the inhibition effect. For example, if a particular electrolyte or cell type is found to inhibit the desired activity of a CAB and is present in a higher concentration in the microenvironment of a normal cell than in a tumor microenvironment, then the desired activity can be triggered by selecting higher concentrations of that electrolyte or cell type for the second value of the condition than for the first value of the condition.

The conditions found in a tumor microenvironment are known to skilled persons from, for example, Gillies et al., "MRI of the Tumor Microenvironment," *JOURNAL OF MAGNETIC RESONANCE IMAGING*, vol. 16, pp. 430-450, 2002, as well as Swarts et al. "Tumor Microenvironment Complexity: Emerging Roles in Cancer Therapy," *Cancer Res*, vol., 72, pp. 2473-2480, 2012, and Estrella et al., "Acidity Generated by the Tumor Microenvironment Drives Local Invasion," *Cancer Res.*, vol. 73, pages 1524-1535, 2013; Lorusso et al., "The tumor microenvironment and its contribution to tumor evolution toward metastasis," *Histochem Cell Biol*, vol. 130, pages 1091-1103, 2008; the disclosures of which are incorporated herein by reference herein in their entirety and for the purpose of describing conditions found in a tumor microenvironment. Certain conditions found in the tumor microenvironment are different from normal physiological conditions of the same subject. The normal physiological conditions are those found, for example, in normal tissue, blood or another normal environment of the subject, e.g. where no tumor is present. The influence of tumors is also described in Mayers et al., "Elevated circulating branched chain amino acids are an early event in pancreatic adenocarcinoma development," *Nature Medicine*, vol. 20, pp. 1193-1198, 2014.

Tumor cells can influence their microenvironment in several ways. For example, it is known that the microenvironment of tumor cells may have a different pH, temperature and/or oxygen partial pressure than the normal physiological conditions of the subject. Tumor cells may also influence their environment by releasing extracellular signals, promoting tumor angiogenesis and inducing peripheral immune tolerance.

The tumor microenvironment is generally hypoxic. As the tumor mass increases, the interior of the tumor grows becomes away from the blood supply, which leads to difficulties in fully supplying oxygen to the interior of the tumor. As a result, the partial oxygen pressure in the tumor microenvironment is typically below 5 mm Hg in more than 50% of locally advanced solid tumors. In comparison, the partial oxygen pressure is typically about 40 mm Hg in blood plasma in veins. Other parts of the body are not typically hypoxic under normal physiological conditions. The hypoxic tumor microenvironment leads to genetic instability, which is associated with cancer progression, via downregulating nucleotide excision repair and mismatch repair pathways. Hypoxia also causes the upregulation of hypoxia-inducible factor 1 alpha (HIF1-α), which induces angiogenesis, and is associated with poorer prognosis and the activation of genes associated with metastasis. See Weber et al., "The tumor microenvironment," *Surgical Oncology*, vol. 21, pages 172-177, 2012 and Blagosklonny, "Antiangiogenic therapy and tumor progression," *Cancer Cell*, vol. 5, pages 13-17, 2004.

In addition, the tumor microenvironment also has an acidic pH (pH 6.0-7.0 or 6.2-6.8), in contrast to other parts of the body which are typically either neutral or slightly basic. For example, human blood plasma has a normal physiological pH of about 7.4. See Estrella et al., "Acidity Generated by the Tumor Microenvironment Drives Local Invasion," *Cancer Research*, vol. 73, pages 1524-1535, 2013.

The tumor microenvironment has also been found to have a higher concentration of lactic acid that is found in a normal physiological environment. The higher lactic concentration is a result of lactic acid fermentation by the tumor cells. Lactic acid fermentation is a process by which the tumor cells using glucose under anaerobic conditions. This process breaks down glucose anaerobically to produce pyruvate, which is eventually converted to lactic acid. A simple equation for lactic acid fermentation is glucose→2 pyruvate→2 lactic acid.

The nutrient availability in the tumor microenvironment has also been found to be typically lower than the nutrient availability in a normal physiological environment. This may be due to the relatively high nutrient demand of the proliferating tumor cells in comparison with cells located in other parts of the body. In particular, the glucose concentration is typically lower in the tumor microenvironment, namely, at a concentration of from about 0.05 mM to about 0.5 mM. In comparison, the normal physiological blood glucose concentration is from about 2.5 mM to about 10 mM.

Further, the tumor microenvironment also contains many distinct cell types or distinct concentrations of particular cell types not commonly found in other parts of the body. These cell types include certain types of endothelial cells and their precursors, pericytes, smooth muscle cells, Wbroblasts, carcinoma-associated Wbroblasts, myoWbroblasts, neutrophils, eosinophils, basophils, mast cells, T and B lymphocytes, natural killer cells and antigen presenting cells (APC) such as macrophages and dendritic cells (Lorusso et al., "The tumor microenvironment and its contribution to tumor evolution toward metastasis," *Histochem Cell Biol*, vol. 130, pages 1091-1103, 2008). In some embodiments, the presence or absence of a particular cell type or different concentrations of a type of cell may be used as the first and second values of the condition.

The first value of the condition may be the presence or concentration of a particular cell type in a tumor microenvironment. In such case, the second value of the condition could be the absence of that particular cell type or a lower concentration of that particular cell type. Such first and second values would be selected if the cell type promotes the activity of the CAB.

The first value of the condition may be the absence of or a particular concentration of a particular cell type in a tumor microenvironment. In such case, the second value of the condition could be the presence of that particular cell type or a higher concentration of that particular cell type than the concentration for the first value of the condition. Such first and second values would be selected if the cell type inhibits the activity of the CAB.

The concentrations of various electrolytes present a tumor microenvironment may also differ from the concentrations of the same electrolytes that are found in a normal physiological environment. In some embodiments, the electrolyte concentrations used for the first and second values of the condition are selected from an ion concentration of calcium, sodium, potassium, magnesium, chloride, bicarbonate or phosphate ions.

Some techniques that may be used to measure the conditions of a tumor microenvironment have been described previously. Measuring partial pressure of oxygen is described in Sakadzic et al., "Two-photon high-resolution measurement of partial pressure of oxygen in cerebral vasculature and tissue," *Nature Methods*, vol. 7, pp. 755-759, 2010 (incorporated hereby by reference). Measuring of pH in a tumor microenvironment is described in Gillies et al., "MRI of the Tumor Microenvironment," *Journal of Magnetic Resonance Imaging*, vol. 16, pp. 430-450, 2002. Measuring temperature in a soft tissue is described in Benjamin et al., "Measurement of soft tissue temperature and impedance following the application of transdermal direct current," *Physiotherapy*, vol. 93, pp. 114-120, 2007. Measuring glucose concentration in a tissue is described in Dunn-Meynell, et al., "Relationship among Brain and Blood Glucose Levels and Spontaneous and Glucoprivic Feeding," *The Journal of Neuroscience*, vol. 29, pp. 7015-7022, 2009. Measuring of lactic acid is described in Hur et al., "Quantitative Measurement of Organic Acids in Tissues from Gastric Cancer Patients Indicates Increased Glucose Metabolism in Gastric Cancer," PLoS ONE, vol. 9:e98581, 2014.

Accordingly, the tumor microenvironment has at least several conditions that are different from conditions found in other parts of body. In the present invention, the CABs rely on at least one of these differences in conditions as a trigger for increasing the activity of the CAB in a particular environment.

In the present invention, a sample is taken from a subject and encapsulated in a capsule shell. The sample may contain one or more CTCs depending on the current state of the subject from which the sample was taken. Thus, if the sample contains one or more CTCs, these CTCs are encapsulated in the capsule shell. The encapsulated CTCs of the invention, since they are still viable, will or can be induced to alter the micro environment within the capsule to generate one or more conditions typically found in a tumor microenvironment. As a result, the interior of the capsule will become a tumor microenvironment if one or more CTCs are present in the encapsulated sample.

A capsule containing encapsulated CTCs is referred to herein as a "CTC capsule." A capsule that does not have CTCs encapsulated therein is herein referred to as a "CTC-free capsule." The CTC capsule will have an internal microenvironment that is different from the normal physiological microenvironment of the CTC-free capsule. The CAB is designed to bind to a cell surface protein on an encapsulated CTC in the CTC capsule when at least condition of a tumor microenvironment is also present. Since the CAB is designed to have a higher activity in the tumor microenvironment than in a normal physiological microenvironment, this will reducing binding of the CAB to the same cell surface protein on cells in the CTC-free capsule where the normal physiological environment is present. Therefore, the CAB is more selective for detection of CTCs because of the influence of a condition of the tumor microenvironment in the CTC capsule on the activity of the CAB.

The difference between the first and second values of the condition may be small if the CAB has a sufficiently high selectivity to enable differentiation of its binding to the cell surface protein under the first and second values of the condition. When the first and second values of the condition are pHs, the difference between them may be as small as about 0.3 pH unit, about 0.5 pH unit, or about 0.7 pH unit, or about 0.8 pH unit, or about 1 pH unit, or about 1.5 pH units, or about 2.0 pH units. When the first and second values of the condition are oxygen partial pressures, the difference between them may be as small as about 5 mmHg, or about 7 mmHg, or about 9 mmHg, or about 10 mmHg, or about 12 mmHg, or about 15 mmHg, or about 20 mmHg, or about 25 mmHg, or about 30 mmHg.

The CAB is more active under the first value of the condition of the tumor microenvironment than under the second value of the condition. In one aspect, the activity of the CAB refers to its binding affinity for binding to a cell surface protein. In this aspect, the CAB will typically have a significantly higher binding affinity for binding a particular cell surface protein found on CTCs under the first value of the condition that the binding higher affinity for binding to the same cell surface protein under the second value of the condition. The ratio of activity of the CAB under the first value of the condition to the activity of the same CAB under the second value of the condition may be at least about 5, or at least about 10, or at least about 20, or at least about 50, or at least about 70, or at least about 100, or at least about 200, or at least about 500, or at least about 700, or at least about 1000. Therefore, in some embodiments, the CAB is selected to have a higher binding affinity to the cell surface protein of a CTC under a first value of the condition that is present in a tumor microenvironment, in comparison with the binding affinity to the same cell surface protein at a second value of the condition that is different from the condition in the tumor microenvironment. The condition is selected from pH, oxygen partial pressure, nutrient levels, electrolyte concentrations, osmotic pressure levels, oxidation stress levels, osmolality levels.

The second value of the condition may be any normal physiological condition. However, in some rare cases, a normal physiological condition may vary from one location in a subject to another location. In embodiments of the present invention, the condition, which represents a normal physiological condition, is selected to be a condition that is expected to exist in a CTC-free capsule containing an encapsulated sample from a subject. Thus, if the sample from the subject is a blood sample, the second value of the condition will be selected to be a normal physiological condition found in a blood sample such as blood plasma. If the sample from the subject is a different sample, such as a cerebrospinal fluid sample, then the second value of the condition should be selected to be a normal physiological condition found in a cerebrospinal fluid sample.

Thus, the present invention takes advantage of the creation of a simulated tumor microenvironment in the CTC capsules, in contrast with the microenvironment found in the CTC-free capsules to improve the selectivity of the method. The present invention is therefore capable of using an antibody to a cell surface protein that is not cancer specific, i.e., it may be present on the surface of CTCs as well as non-tumor cells. Since the binding affinity of the CAB to the cell surface protein is influenced by a condition in the microenvironment, the CAB will have a higher binding affinity for the cell surface protein on CTCs because of the tumor microenvironment that the CTCs create in the capsule. The present invention is thus capable of using CAB to identify the presence of CTCs which CAB can bind to a cell surface protein found both in CTCs and non-CTCs. This approach is in contrast to known methods where antibodies to cancer specific markers are required because there is no secondary factor that prevents binding of the antibody to a marker found on a non-CTC. Further, the requirement of both the presence of the cell surface protein and a condition of a tumor microenvironment in the capsule provides additional assurance against false positive results.

Thus, in some embodiments, the present invention may employ a CAB with a binding affinity for a cell surface protein is present on both a CTC and a non-CTC from the subject. This is because the secondary factor, namely the condition in the microenvironment, can be used to reduce binding to cell surface proteins present on non-CTCs. Suitable cell surface proteins may be selected from, for example, proteins of housekeeping genes. In some other embodiments, the cell surface protein may be a protein present on CTCs of most major cancer types, but not on rare or non-tumor cancer cells. The major cancer types include breast cancer, lung cancer, colorectal cancer, pancreatic cancer, prostate cancer, bladder cancer, kidney cancer, endometrial cancer, leukemia, melanoma, non-Hodgkins lymphoma and thyroid cancer.

In some embodiments, the cell surface protein may be selected from cell membrane proteins such as ABCA7, ABCC1, ABCC5, ABHD3, ACKR3, ADAM10, AQP1, AQP3, ATP13A3, ATP1B3, ATP2B1, ATP2B4, ATP6AP1, ATP6V0A2, BACE1, BMPR2, BNIP2, BST2, BTN2A1, BTN3A3, C12orf76, C17orf62, C1orf27, CCDC107, CD4, CD44, CD46, CD81, CD9, CD99L2, CDAN1, CDIPT, CLCN6, CNNM4, CYP20A1, DCBLD2, DHRS7B, ERBB2, ETNK1, FAM210B, GINM1, GPI, GRAMD1A, HELZ, HERPUD1, HMOX1, HPS3, ICAM1, IFI30, IFRD1, IL15RA, IL6ST, ITGA7, ITGB1, ITGB4, ITGB5, ITSN1, JAG1, LAIR1, LMTK2, LRBA, LRP12, LSR, MACF1, MADD, MCAM, MCOLN1, MET, MICAL3, MPV17L2, NCKIPSD, NDC1, NEO1, NOTCH2, PANX1, PDLIM5, PFDN1, PGAP3, PGRMC2, PHLDB2, PIGN, PIGQ, PIGW, PKN2, PTPRS, PVR, RALGAPA2, RNF145, RNF149, SC5D, SCAMP4, SDC2, SDC4, SLC12A2, SLC16A1, SLC16A3, SLC17A5, SLC19A1, SLC1A5, SLC30A1, SLC38A6, SLC38A7, SLC39A114, SLC3A2, SLC43A1, SLC46A1, SLC46A3, SLC4A2, SLC4A7, SLC7A5, SLC9A1, SMAGP, SORT1, SPG11, SPINT2, SPPL2B, SPPL3, SRD5A3, SRPRB, STX18, STX4, SYVN1, TAPT1, TAZ, TBC1D5, TGFBR2, TM2D2, TMEM183A, TMEM205, TMEM218, TMEM222, TMEM245, TMEM258, TMEM50A, TMEM63B, TMEM97, TNFRSF12A, TXNDC11, UBR2, UQCC1, VSIG4, WWP1, YIPF4, ZDHHC20 and ZDHHC5. More information on the genes that encode these proteins may be found at http://www.proteinatlas.org/.

In some embodiments, the cell surface protein may be a protein encoded by housekeeping genes. Examples of such proteins are AP2S1, CD81, GPAA1, LGALS9, MGAT2, MGAT4B and VAMP3. In one embodiment, the cell surface protein is a protein from the SLC2a family of housekeeping genes. Examples of cell surface proteins of the SLC2a family include SLC2A1, SLC2A2, SLC2A3, SLC2A4, SLC2A5, SLC2A6, SLC2A7, SLC2A8, SLC2A9, SLC2A10, SLC2A11, SLC2A12, SLC2A13, and SLC2A14.

In one embodiment, the cell surface protein is Axl, which is present on CTCs from most cancer types, though not all of the major cancer types. Axl is a particularly suitable target for the present invention if the goal is to identify the presence of one or more cancers which have cells containing the Axl cell surface protein.

The CAB for a cell surface protein may be screened and selected using any methods as discussed herein. Once selected, the CAB may be commercially produced through using recombinant techniques or protein synthesis techniques. The CAB can be recombinantly expressed in vitro or in vivo using any method known in the art. The CAB can also be synthesized, whole or in part, using chemical methods. The production of CABs has been described in WO2010104821A1, which is hereby incorporated by reference herein for the purpose of describing how to produce CABs.

In some embodiments, the CAB may be engineered with one or more protein engineering techniques described herein. Non-limiting examples of protein engineering techniques include antibody conjugation and engineering multispecific antibodies.

The CAB may be conjugated to a detectable label. Examples of detectable labels include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties.

The conjugation of the CAB to the detectable label can be covalent conjugation or non-covalent conjugation. Covalent conjugation can either be direct or via a linker. In certain embodiments, direct conjugation is by construction of a fusion protein (i.e., by genetic fusion of the two genes encoding the CAB and neurological disorder drug and expression as a single protein). In certain embodiments, direct conjugation is by formation of a covalent bond between a reactive group on one of the two portions of the CAB and a corresponding group or acceptor on the detectable label. In certain embodiments, direct conjugation is by modification (i.e., genetic modification) of one of the two molecules to be conjugated to include a reactive group (as non-limiting examples, a sulfhydryl group or a carboxyl group) that forms a covalent attachment to the other molecule to be conjugated under appropriate conditions. As one non-limiting example, a molecule (i.e., an amino acid) with a desired reactive group (i.e., a cysteine residue) may be introduced into, e.g., the CAB and a disulfide bond formed with the neurological drug. Methods for covalent conjugation of nucleic acids to proteins are also known in the art (i.e., photocrosslinking, see, e.g., Zatsepin et al. *Russ. Chem. Rev.*, 74: 77-95 (2005)). Non-covalent conjugation can be by any non-covalent attachment means, including hydrophobic bonds, ionic bonds, electrostatic interactions, and the like, as will be readily understood by one of ordinary skill in the art.

Conjugation may also be performed using a variety of linkers. For example, a CAB and the detectable label may be conjugated using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Peptide linkers, comprised of from one to twenty amino acids joined by peptide bonds, may also be used. In certain such embodiments, the amino acids are selected from the twenty naturally-occurring amino acids. In certain other such embodiments, one or more of the amino acids are selected from glycine, alanine, proline, asparagine, glutamine and lysine. Some examples of crosslinker reagents for antibody conjugation include BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate)

The detectable labels can be conjugated to the CAB may also include any diagnostic agent known in the art, as provided, for example, in the following references: Armstrong et al, Diagnostic Imaging, 5$^{th}$ Ed., Blackwell Publishing (2004); Torchilin, V. P., Ed., Targeted Delivery of Imaging Agents, CRC Press (1995); Vallabhajosula, S., Molecular Imaging: Radiopharmaceuticals for PET and SPECT, Springer (2009). A diagnostic agent can be detected by a variety of methods, including using the agent to provide and/or enhance a detectable signal that includes, but is not limited to, gamma-emitting, radioactive, echogenic, optical, fluorescent, absorptive, magnetic or tomography signals. Techniques for imaging the diagnostic agent can include, but are not limited to, single photon emission computed tomography (SPECT), magnetic resonance imaging (MRI), optical imaging, positron emission tomography (PET), computer tomography (CT), x-ray imaging, gamma ray imaging, and the like.

In some embodiments, the detectable label may be chelators that bind, e.g., to metal ions to be used for a variety of diagnostic imaging techniques. Exemplary chelators include but are not limited to ethylenediaminetetraacetic acid (EDTA), [4-(1,4,8,11-tetraazacyclotetradec-1-yl) methyl]benzoic acid (CPTA), Cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7,10-tetraazacyclododecane-1,4,7,10-tetra (methylene phosphonic acid) (DOTP), 1,4,8,11-tetraazacyclododecane-1,4,8,11-tetraacetic acid (TETA), 1,4,7, 10-tetraazacyclododecane-1,4,7,10-tetraacetic acid (DOTA), and derivatives thereof.

In some embodiments, the detectable label may be radioisotope including radionuclides that emit gamma rays, positrons, beta and alpha particles, and X-rays. Suitable radionuclides include but are not limited to Ac, As, At, $^n$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{123}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga. In some embodiments, the liposomes can be radiolabeled, for example, by incorporation of lipids attached to chelates, such as DTPA-lipid, as provided in the following references: Phillips et al, Wiley Interdisciplinary Reviews: *Nanomedicine and Nanobiotech-*

*nology*, vol. 1, pages 69-83 (2008); Torchilin, V. P. & Weissig, V., Eds. Liposomes 2nd Ed.: Oxford Univ. Press (2003); Elbayoumi, T. A. & Torchilin, V. P., *Eur. J. Nucl. Med. Mol. Imaging*, 33: 1196-1205 (2006); Mougin-Degraef, M. et al, *Int'l J. Pharmaceutics*, 344: 110-117 (2007).

In other embodiments, the detectable label may include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives having the general structure of 4,4-difluoro-4-bora-3a,4a-diaza-s-indacene, and/or conjugates and/or derivatives of any of these. Other agents that can be used include, but are not limited to, fluorescein, fluorescein-polyaspartic acid conjugates, fluorescein-polyglutamic acid conjugates, fluorescein-polyarginine conjugates, indocyanine green, indocyanine-dodecaaspartic acid conjugates, indocyanine (NIRD)-polyaspartic acid conjugates, isosulfan blue, indole disulfonates, benzoindole disulfonate, bis(ethylcarboxymethyl)indocyanine, bis(pentylcarboxymethyl)indocyanine, polyhydroxyindole sulfonates, polyhydroxybenzoindole sulfonate, rigid heteroatomic indole sulfonate, indocyaninebispropanoic acid, indocyaninebishexanoic acid, 3,6-dicyano-2,5-[(N,N,N',N'-tetrakis (carboxymethyl)amino]pyrazine, 3,6-[(N,N,N',N'-tetrakis (2-hydroxyethyl)amino]pyrazine-2,5-dicarboxylic acid, 3,6-bis(N-azatedino)pyrazine-2,5-dicarboxylic acid, 3,6-bis(N-morpholino)pyrazine-2,5-dicarboxylic acid, 3,6-bis(N-piperazino)pyrazine-2,5-dicarboxylic acid, 3,6-bis(N-thiomorpholino)pyrazine-2,5-dicarboxylic acid, 3,6-bis(N-thiomorpholino)pyrazine-2,5-dicarboxylic acid S-oxide, 2,5-dicyano-3,6-bis(N-thiomorpholino)pyrazine S,S-dioxide, indocyaninetetrasulfonate, chloroindocarbocyanine, and 3,6-diaminopyrazine-2,5-dicarboxylic acid.

In yet other embodiments, the detectable label may include contrast agents that are generally well known in the art, including, for example, superparamagnetic iron oxide (SPIO), complexes of gadolinium or manganese, and the like. (See, e.g., Armstrong et al, Diagnostic Imaging, 5$^{th}$ Ed., Blackwell Publishing (2004)). In some embodiments, a diagnostic agent can include a magnetic resonance (MR) imaging agent. Exemplary magnetic resonance agents include but are not limited to paramagnetic agents, superparamagnetic agents, and the like. Exemplary paramagnetic agents can include but are not limited to Gadopentetic acid, Gadoteric acid, Gadodiamide, Gadolinium, Gadoteridol, Mangafodipir, Gadoversetamide, Ferric ammonium citrate, Gadobenic acid, Gadobutrol, or Gadoxetic acid. Superparamagnetic agents can include but are not limited to superparamagnetic iron oxide and Ferristene. In certain embodiments, the diagnostic agents can include x-ray contrast agents as provided, for example, in the following references: H. S Thomsen, R. N. Muller and R. F. Mattrey, Eds., Trends in Contrast Media, (Berlin: Springer-Verlag, 1999); P. Dawson, D. Cosgrove and R. Grainger, Eds., Textbook of Contrast Media (ISIS Medical Media 1999); Torchilin, V. P., *Curr. Pharm. Biotech.*, vol. 1, pages 183-215 (2000); Bogdanov, A. A. et al, *Adv. Drug Del. Rev.*, Vol. 37, pages 279-293 (1999); Sachse, A. et ah, *Investigative Radiology*, vol. 32, pages 44-50 (1997). Examples of x-ray contrast agents include, without limitation, iopamidol, iomeprol, iohexol, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol. In certain embodiments, the x-ray contrast agents can include iopamidol, iomeprol, iopromide, iohexol, iopentol, ioversol, iobitridol, iodixanol, iotrolan and iosimenol.

The CAB of the present invention may be engineered to generate a multispecific CAB. Mutispecific CABs and methods for making them are described in WO 2013/170168, incorporated herein by reference in its entirety. Multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains where each $V_H V_L$ unit binds to a different epitope, antibodies having two or more single variable domains with each single variable domain binding to a different epitope, and antibodies comprising one or more antibody fragments as well as antibodies comprising antibody fragments that have been linked covalently or non-covalently.

In one embodiment, multispecific antibodies can be engineered to have binding affinities for two or more cell surface proteins that are found on different types of cancer cells. In this manner, a single multispecific antibody can be engineered to target difference cancer cell types in cases where the different cancer cells express different cell surface proteins. This type of engineering may be useful for screening of patients for a variety of different types of cancer in a single test.

Multispecific antibodies can be engineered for binding affinity to one or more target CTCs with all or most of the targets (cell surface proteins) that a multispecific antibody can bind to. For example, a bispecific antibody may be engineered to provide selectivity for certain target cells by engineering the CAB to bind to two different cell surface proteins that are expressed by the same target cell, in comparison with non-target cells that may express only one or none of these two cell surface proteins. Therefore, due to the dynamism of the system, more bispecific antibodies can be bound to the target cells than non-target cells at equilibrium using this approach.

These two protein engineering techniques may be used in the present invention. Conjugating a detectable label to the CAB permits detection of the CTCs after the CAB is bound to the cell surface protein on the CTCs. Multispecific CABs permit targeting of multiple cell surface proteins which can all be bound to a single multispecific CAB. This may be advantageous because the targeting of more than one cell surface protein may provide the ability to detect broader spectrum of cancers. For example, each cell surface protein enables detection of overlapping sets of cancers, the sum of all the sets of cancers is a larger set cover a broader spectrum of cancers which can be detected by using the multispecific CAB.

Thus, the present invention provides a simplified method for detecting CTCs in a sample from a subject using just a single antibody by encapsulating 50 the CTCs in a capsule whose internal environment will be changed to be same or similar to a tumor microenvironment (FIG. 1).

In some embodiments, the CTCs in the sample obtained from a subject in step 10 of the method of FIG. 1 may be at a concentration too low for detection. Two steps may be used to increase the CTC population in the sample alone or in combination: (1) either expanding 20 the CTC population in the fluid or (2) enriching 30 the CTC population in the fluid (FIG. 1).

Expanding 20 the CTC population means preferentially increasing the number of CTCs in the sample (i.e., new CTCs are generated) relative to an increase in the number of other non-CTCs. Expanding 20 the CTC population may be accomplished by culturing the entire cell population from the sample under conditions suitable for preferential expansion 20 of CTC population. In the case of some cancer cells this result may be achievable using any suitable cell culture medium since certain types of cancer cells proliferate faster than other types of cells that may be present in the sample. As a result, the CTC population of cells that are known to proliferate faster than other cells can be expanded 20 merely by culturing the entire cell population.

The entire cell population can be cultured in any suitable type of culture, such as a suspension culture, spheroid culture or cultured in a matrix. Any coated or uncoated vessel, flask, or three-dimensional extracellular matrix that facilitates cell attachment, growth, differentiation, migration, and tissue morphogenesis can be used. For example, the matrix may be methylcellulose, carboxymethylcellulose, collagen, Matrigel™ (basement membrane preparation extracted from the Enelbreth-Holm-Swam mouse sarcoma; BD Biosciences), and the like.

In one embodiment, the entire cell population is from a peripheral blood sample of a subject. The cell population is added into a medium and cultured under conditions suitable for preferential expansion of CTCs (e.g., 5% $CO_2$, 37° C. incubator). The cell population may be cultured for about 1 week, about 2 weeks, about 3 weeks, about 4 weeks, about 1-2 weeks, or about 2-4 weeks to accomplish the desired level of CTC expansion.

The culture media can be any media suitable for growth of mammalian (e.g., human) cells, and typically contain salts, amino acids and other nutrients, and can be supplemented with antibiotics, and other components if desired. Many suitable media formulations are well known and conventional in the art, such as RPMI media, Knockout serum replacement media, F12K, and DMEM. The culture media is preferably supplemented with a low concentration of serum, plasma or growth factors (i.e. 5% or less (v/v) serum or plasma) or is serum or plasma free. These conditions favor the growth of tumor cells (CTCs) under epithelial to mesenchymal transition (or "stem cell-like") conditions. On the other hand, the white blood cells in the fluid will not proliferate under these conditions without addition of specific growth factors and higher serum concentration.

The cell culture media may comprise about 0.1% to about 5%, about 0.1% to about 4%, about 0.1% to about 3% serum or plasma (e.g., human serum or plasma), about 0.5% to about 2.5%, about 1% to about 2%, about 0.5%, about 0.6%, about 0.7%, about 0.8%, about 0.9%, about 1.0%, about 1.2%, about 1.4%, about 1.6%, about 1.8%, about 2.0%, about 2.2%, about 2.4%, about 2.6%, about 2.8% or about 3% serum or plasma (e.g., human serum or plasma). The culture media preferably is supplemented with from about 1.0% to about 2.0% of human serum or plasma. The culture media may also be serum free.

Suitable culture conditions may comprise incubation at about 35° C. to about 40° C. (e.g., about 36° C., about 37° C., about 38° C., about 39° C.) in a humidified atmosphere (e.g. 95% relative humidity) that contains about 3% to about 7% carbon dioxide (e.g., about 5% carbon dioxide).

For enrichment 30 of CTCs, no substantial new CTCs are generated in the sample but instead the relative population of CTCs is increased relative to the population of other non-CTCs in the sample. Enrichment 30 may be used to increase the relative amount of revealed CTCs in a sample by 25%, 50%, 100%, 200%, 500% or more.

Enrichment 30 of CTCs in a peripheral blood sample may be accomplished using techniques designed to remove red blood cells and/or other types of non-CTCs typically found in a blood sample using one or more conventional separation techniques (e.g., fractionation, red blood cell lysis, cell sorting, filtration, adhesion, density centrifugation, ammonium chloride lysis). For example, red blood cells can be removed from a whole blood sample by density gradient sedimentation. However, care should be taken when employing enrichment methods that can result in cellular damage since viable CTCs need to be preserved in the enriched sample.

In some embodiments, enrichment 30 may be based on physical characteristics of CTCs, such as shape, size, density or electrical charge (Vona et al., "Isolation by size of epithelial tumor cells—A new method for the immunomorphological and molecular characterization of circulating tumor cells," *American Journal Of Pathology*, vol. 156, pp. 57-63, 2000). In one embodiment, the CTCs may be enriched using filtration. The filtration is particularly effective in enriching 30 revealed CTCs since revealing the CTCs breaks down aggregates of cells, thereby making the filtration more efficient.

In some embodiments, the CTCs in the sample, optionally expanded 20 and/or enriched 30, may be treated to reveal 40 the cell surface protein thereon (FIG. 1). It was discovered that significant numbers of CTCs in circulation remain undetectable because they are "masked" or "cloaked" by cells, proteins, biomolecules and other factors aggregated at the surface of the CTCs shielding them from being detected by the CAB. For example, platelets, fibrin, and other clotting proteins act as a "cloak device" to mask or veil the cell surface proteins, allowing them to escape detection. Similarly, other factors can effectuate masking or veiling of CTCs such as, for example, glycosylation of surface protein markers or association of cell surface components with other biomolecules, such as lipids. The step of revealing the CTCs may include removing, degrading or altering proteins, carbohydrates, cells, or a combination thereof, aggregated, or in physical association with, the surface of the CTCs. One or more of the cell surface proteins of the revealed CTCs will then be more easily accessible by the CAB than it was before the revealing step was carried out.

Suitable techniques for revealing 40 the CTCs may include treating the cells enzymatically (e.g., biochemical reaction mediated by an enzyme), mechanically (e.g., mechanical force), electrically (e.g., electrical force), electromagnetically (e.g., electromagnetic radiation of the electromagnetic spectrum), chemically, or any combination thereof to remove or alter platelets, proteins, carbohydrates, cells or other biomolecules associated with the surface of the CTCs to reveal 40 the cell surface protein.

In some embodiments, degradation of the clotting proteins and/or cells from the surface of a CTC is performed by treating the CTCs enzymatically. Enzymatic treatment may occur by fibrinolysis, which is an enzymatic process wherein fibrin and/or products of coagulation, such as fibrin clots and the like are degraded. In one aspect, degradation by fibrinolysis is performed by treatment of CTCs with the enzyme plasmin. Plasmin is a serine protease present in the blood that degrades fibrin as well as other blood plasma proteins performing a crucial role in fibrinolysis. Plasmin is known to enzymatically cleave proteins such as fibrin, fibronectin, thrombospondin, laminin, and von Willebrand factor. Various natural and synthetic plasmins are known in the art and may be used in the present invention so long as the enzyme retains some role in fibrinolysis.

Plasmin is derived from plasminogen which is excreted from the liver into the circulation. Once in the circulation, plasminogen may be activated by a variety of factors to generate plasmin, such as tissue plasminogen activator (tPA), urokinase plasminogen activator (uPA), thrombin, fibrin, and factor XII (Hageman factor). Accordingly, in some embodiments of the invention, fibrinolysis is produced by enzymatic activation of plasminogen. Fibrinolysis may also be effectuated by other naturally or synthetically occurring agents. For example, the fibrinolysis may occur by treatment of CTCs with a natural or synthetic animal venom or toxin. For example, venomous animals, such as but not limited to bats, snakes and insects are known to possess venom or toxins capable of direct or indirect enzymatic activation of fibrinolysis.

In addition to enzymatic degradation of clotting proteins and cells on the surface of masked CTCs, CTCs may also be treated mechanically, electrically, or chemically. For example, mechanical forces may be used in the treatment of CTCs to shear the clotting proteins and cells on the surface of CTCs. Accordingly, the CTCs may be treated with any type of mechanical force or movement capable of unmasking CTCs. Additionally, treatment of CTCs with a variety of electrical forces may be utilized to unmask CTCs such as, but not limited to, electromagnetic, electrostatic, electrochemical, electroradiation, ultrasonic forces, and the like. Electromagnetic radiation may include application of radiation from any region of the electromagnetic spectrum.

In one embodiment, the mechanical forces may be generated in microfluidic devices used for biomedical and diagnostic research. The microscale devices that constitute a microfluidic system typically consist of a plurality of posts, grooves or microchannels, and chambers etched or molded in a substrate commonly composed of silicon, plastic, quartz, glass, or plastic. The size, shape, configuration of these microscale features, as well as their interconnections determine the physical forces generated on the constituents of a fluid sample flowing through the device, such as cells or clusters of cells suspended in the fluid. It is contemplated that the microscale features of a microfluidic device, along with factors, such as rate of fluid flow, may be configured and exploited to generate sufficient mechanical forces to reveal CTCs in a fluid sample.

Chemical treatments for revealing 40 CTCs uses chemical agents such as, but not limited to, natural or synthetic molecules, organic compounds, non-organic compounds, drugs, therapeutics, and the like may activate or inhibit various steps in the fibrinolysis pathway leading to degradation of clotting factors. Additional chemical agents that may be used to unmask CTCs include anti-platelets, anti-coagulants and/or blood thinners which degrade and/or suppress the platelet and fibrin activation on the surface of CTCs. Common anti-platelets, anti-coagulants and blood thinners that may be used include but are not limited to, cyclooxygenase inhibitors, such as aspirin; adenosine diphosphate (ADP) receptor inhibitors, such as clopidogrel, and ticlopidine; phosphodiesterase inhibitors, such as cilostazol; glycoprotein IIB/IIIA inhibitors, such as abciximab, eptifibatide, tirofiban, and defibrotide; adenosine reuptake inhibitors such as dipyridamole; vitamin K antagonists; heparin and heparin derivative substances; clopidogrel (Plavix™); benzopyrone (coumarin); and direct thrombin inhibitors.

It is important to select the treatment and/or limit the duration of treatment in the revealing 40 step to avoid impairing the viability or integrity of the CTCs and to avoid damage the cell surface protein intended to be bound by the CAB. Accordingly, in various embodiments, cells should be treated for a time sufficient for removing clotting proteins/cells from the CTCs so that the CTCs can be further detected and/or identified. While this time may vary depending of the type of treatment applied to the CTCs, it is within the knowledge of one skilled in the art to determine such time by routine assays. Additionally, where CTCs are treated enzymatically or chemically, the duration of the enzymatic reactions may be controlled by addition of specific inhibitors to slow or stop such reactions.

The total number of revealed 40 CTCs included in a treated sample is dependent, in part, on the initial sample volume. The initial sample volume may be less than about 25 µl, 50 µl, 75 µl, 100 µl, 125 µl, 150 µl, 175 µl, 200 µl, 225 µl, 250 µl, 300 µl, 400 µl, 500 µl, 750 µl, 1 ml, 2 ml, 3 ml, 4 ml, 5 ml, 6 ml, 7 ml, 8 ml, 9 ml or greater than about 10 ml. In an exemplary aspect, the initial sample volume is between about 100 and 200 µl. In another exemplary aspect, a sample after the revealing 40 step as described herein includes greater than about 1, 2, 5, 7, 10, 15, 20, 30, 40, 50, 100, 200, 300, 400, 500, 600, 700, 800, 900, or even 1000 revealed CTCs. In some embodiments, the treated sample has greater than about 5, 7.5, 10, 50, 100, or 200 revealed CTCs per 100 microliters of sample.

The sample containing the CTCs, which may be expanded 20 or unexpanded, enriched 30 or unenriched, revealed 40 or unrevealed, or any combination thereof, is encapsulated 50 in capsules. The CTCs to be encapsulated 50 are suspended in an aqueous media, either in the sample or a portion of thereof itself, or in the sample or a portion thereof optionally supplemented with nutrients or in a different aqueous media. Cell encapsulation is a well-known technology where an aqueous media is reduced to emulsified aqueous droplets followed by encapsulating the droplets with semipermeable membranes made by depositing polymer around the droplets, either by coacervation or interfacial polymerization. The core of the capsule is the aqueous media having one or more CTCs suspended therein and may include other components of the sample, as well as additional added components such as growth media, nutrients, etc. The shell is typically a semipermeable membrane. This encapsulation process is described, for example, in U.S. Pat. No. 5,573,934, hereby incorporated by reference herein.

Other suitable cell encapsulation methods have been disclosed previously, including at least in U.S. Pat. Nos. 4,353,888; 4,391,909; 4,689,293; 4,803,168; 4,806,355; 5,227,298; 6,790,455; 6,818,230; 7,041,504; 7,297,331; 8,202,701, and U.S. Patent Publication Nos.: 2002/0098559, 2004/0029241, 2004/0086493, 2004/0170612, 2005/0037029, 2005/0118425, 2005/0202096, 2005/0214377, 2006/0251630, 2009/0214660, 2009/0269313, 2011/0064797, 2012/0213708, 2012/0231443, 2012/0308650, 2013/0277872, 2014/0127290 and 2014/0271843, the disclosures of which are hereby incorporated by reference for describing suitable cell encapsulation techniques.

Burgess, D. J. (1994) Complex Coacervation: Microcapsule Formation. In: Dubin, P., Bock, J, Davis, R., Schulz, D. N. and Thies, C. (Eds.), Macromolecular Complexes in Chemistry and Biology, Springer-Verlag, Berlin, Heidelberg, New York, London, Paris, Tokyo, Hong Kong, Barcelona, Budapest, pp. 285-300 describe suitable coacervation methods.

The capsule shell is preferably a biocompatible polymer, which means that the capsule shell, its metabolites or its degradation products are generally non-toxic to the encapsulated cells. Also, the capsule shell should be selected such that the capsule shell, its metabolites or its degradation products do not materially alter that at least one condition of the microenvironment inside the capsule that is selected to trigger the CAB. For example, if the CAB is designed to be triggered by a pH difference, then the capsule shell should be selected so that it will not materially affect the pH of the encapsulated material at least during the time period from encapsulation until final testing.

The polymer used in the capsule shell may be a natural or synthetic polymer. The synthetic polymers that can be used include biodegradable polymers such as poly(lactide) (PLA), poly(glycolide) (PGA), poly(lactide-co-glycolide) (PLGA), poly(caprolactone) (PCL), polycarbonates, polyamides, polyanhydrides, polyphosphazene, polyamino acids, polyortho esters, polyacetals, polycyanoacrylates and biodegradable polyurethanes; non-biodegradable polymers such as polyacrylates, ethylene-vinyl acetate polymers and other acyl-substituted cellulose acetates and derivatives thereof; polyurethanes, polystyrenes, polyvinyl chloride, polyvinyl fluoride, poly(vinyl imidazole), chlorosulphonated polyolefins, and polyethylene oxide. Examples of natural polymers include proteins such as albumin, collagen, synthetic polyamino acids and prolamins; polysaccharides such as alginate, heparin; and other naturally occurring biodegradable polymers of sugar units. Alternately, combinations of the aforementioned polymers can be used.

The shell of the capsule is semipermeable. The porosity of the capsule shell can be controlled by techniques known to those skilled in the art, such as by optimizing the degree of crosslinking of one or more polymers in the shell. A thinner capsule shell will allow solvent to diffuse through the shell more easily than a thicker capsule shell.

In some embodiments, instead of an aqueous media, the core of the capsules may comprise a matrix in which the CTCs or other cells are suspended. The matrix can be cross-linked polymers distributed in an aqueous media, thus making the core a viscous aqueous liquid or a hydrogel. In some embodiments, the core can have a viscosity that is at least two times, four times, six times, eight times, ten times, or twenty times of the viscosity of water at 25° C.

The cross-links between polymeric units forming a hydrogel may be covalent, ionic, or hydrogen bonds to create a three-dimensional open-lattice structure which entraps water molecules to form a hydrogel. In some embodiments, the matrix contains proteins and nutrients suitable for promoting a cell activity, such as survival, and/or growth for the encapsulated CTCs. The protein can be collagen, fibrin, gelatin, elastin, or elastin-like polypeptides (ELPs), or a derivative thereof. The nutrient may be a nutrient osmolyte, which is a solute that is a nutrient for the CTCs and helps maintain the osmotic balance of the solution to protect the CTCs from swelling, bursting, or dehydrating. Glucose is a common nutrient in the osmolyte. The amount of glucose can be from about 30 to about 300 mM, or from about 40 to about 250 mM, or from about 50 to about 200 mM, or from about 70 to about 170 mM, or from about 100 to about 170 mM, or from about 130 to about 150 mM.

Examples of polymers which can be used to form a suitable hydrogel for the core include polysaccharides such as alginate, polyphosphazines, poly(acrylic acids), poly (methacrylic acids), poly(alkylene oxides), poly(vinyl acetate), poly(acrylamides) such as poly(N-isopropylacrylamide), polyvinylpyrrolidone (PVP), and copolymers and blends of each. In some embodiments, block copolymers can be used. For example, poloxamers containing a hydrophobic poly(alkylene oxide) segment (i.e., polypropylene oxide) and hydrophilic poly(alkylene oxide) segment (i.e., polyethylene oxide) can be used.

In some cases, the polymer is selected from anionic polymers such as alginate to form a hydrogel matrix (i.e., core). Alginate can form a gel in the presence of divalent cations via ionic crosslinking, which can be performed by addition of a divalent metal cation (e.g., a calcium ion or a barium ion), or by cross-linking with a polycationic polymer (e.g., an amino acid polymer such as polylysine). The hydrogel matrix can optionally be crosslinked, if desired. The matrix can also be formed from viscous solutions, such as, for example solutions of cellulose and its derivatives (e.g., carboxymethyl cellulose).

In some embodiments, the core, the shell, or both comprise chitosan or derivative thereof. Chitosan is made by partially deacetylating chitin, a natural non-mammalian polysaccharide, which exhibits a close resemblance to mammalian polysaccharides, making it attractive for cell encapsulation. Chitosan degrades predominantly by lysozyme through hydrolysis of the acetylated residues. Higher degrees of deacetylation lead to slower degradation times. Under dilute acid conditions (pH<6), chitosan is positively charged and water soluble, while at physiological pH, chitosan is neutral and hydrophobic, leading to the formation of a solid physically crosslinked hydrogel. The addition of polyol salts enables encapsulation of cells at neutral pH, where gelation becomes temperature dependent.

In some embodiments, the core, the shell, or both comprise hyaluronan or derivative thereof. Hyaluronan (HA) is a glycosaminoglycan present in many tissues throughout the body that plays an important role in embryonic development, wound healing, and angiogenesis. In addition, HA interacts with cells through cell-surface receptors to influence intracellular signaling pathways. HA can be modified with crosslinkable moieties, such as methacrylates and thiols, for cell encapsulation. Crosslinked HA gels remain susceptible to degradation by hyaluronidase, which breaks HA into oligosaccharide fragments of varying molecular weights. Auricular chondrocytes can be encapsulated in photopolymerized HA hydrogels where the gel structure is controlled by the macromer concentration and macromer molecular weight. In addition, photopolymerized HA and dextran hydrogels may maintain a long-term culture of undifferentiated human embryonic stem cells. HA hydrogels have also been fabricated through Michael-type addition reaction mechanisms where either acrylated HA is reacted with PEG (Polyethylene Glycol)-tetrathiol, or thiol-modified HA is reacted with PEG diacrylate.

In some embodiments, the core, the shell, or both comprise chondroitin or derivative thereof. Chondroitin sulfate makes up a large percentage of structural proteoglycans found in many tissues, including skin, cartilage, tendons, and heart valves, making it an attractive biopolymer for a range of tissue engineering applications. Photocrosslinked chondroitin sulfate hydrogels can be been prepared by modifying chondroitin sulfate with methacrylate groups.

The hydrogel properties were readily controlled by the degree of methacrylate substitution and macromer concentration in solution prior to polymerization. Further, the negatively charged polymer creates increased swelling pressures allowing the gel to imbibe more water without sacrificing its mechanical properties. Copolymer hydro gels of chondroitin sulfate and an inert polymer, such as PEG or PVA (polyvinyl acetate), may also be used.

In some embodiments, the core, the shell, or both comprise a synthetic polymer or polymers. Polyethylene glycol (PEG) has been the most widely used synthetic polymer to create macromers for cell encapsulation. A number of studies have used poly(ethylene glycol)di(meth)acrylate to encapsulate a variety of cells. Biodegradable PEG hydrogels can be been prepared from triblock copolymers of poly($\alpha$-hydroxy esters)-b-poly(ethylene glycol)-b-poly($\alpha$-hydroxy esters) endcapped with (meth)acrylate functional groups to enable crosslinking poly (lactic acid) (PLA) and poly(8-caprolactone) (PCL) have been the most commonly used poly($\alpha$-hydroxy esters) in creating biodegradable PEG macromers for cell encapsulation. The degradation profile and rate are controlled through the length of the degradable block and the chemistry. The ester bonds may also degrade by esterases present in serum, which accelerates degradation. Biodegradable PEG hydrogels can also be fabricated from precursors of PEG-bis-[2-acryloyloxy propanoate]. As an alternative to linear PEG macromers, PEG-based dendrimers of poly(glycerol-succinic acid)-PEG, which contain multiple reactive vinyl groups per PEG molecule, can be used. An attractive feature of these materials is the ability to control the degree of branching, which consequently affects the overall structural properties of the hydrogel and its degradation. Degradation will occur through the ester linkages present in the dendrimer backbone.

In some embodiments, the core, the shell, or both comprise polyphosphoesters or polyphosphates where the phosphoester linkage is susceptible to hydrolytic degradation resulting in the release of phosphate. For example, a phosphoester can be incorporated into the backbone of a crosslinkable PEG macromer, poly(ethylene glycol)-di-[ethyl-phosphatidyl (ethylene glycol) methacrylate] (PhosPEG-dMA), to form a biodegradable hydrogel. The addition of alkaline phosphatase, an extracellular matrix (ECM) component synthesized by bone cells, enhances degradation. The degradation product, phosphoric acid, reacts with calcium ions in the medium to produce insoluble calcium phosphate inducing autocalcification within the hydrogel. Poly(6-aminoethyl propylene phosphate), a polyphosphoester, can be modified with methacrylates to create multivinyl macromers where the degradation rate was controlled by the degree of derivatization of the polyphosphoester polymer.

In some embodiments, the core, the shell, or both comprise polyphosphazenes that have backbones consisting of nitrogen and phosphorous separated by alternating single and double bonds. Each phosphorous atom is covalently bonded to two side chains. The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized by incorporating monomers having imidazole, amino acid ester, or glycerol side groups. Bioerodible polyphosphazines have at least two differing types of side chains, acidic side groups capable of forming salt bridges with multivalent cations, and side groups that hydrolyze under in vivo conditions, e.g., imidazole groups, amino acid esters, glycerol and glucosyl. Examples of hydrolyzing side chains are unsubstituted and substituted imidazoles and amino acid esters in which the group is bonded to the phosphorous atom through an amino linkage.

The capsules of the present invention may have a diameter 1000 µm or less, which are commonly called microcapsules. For example, the microcapsules may have a diameter of from about 10 µm to about 1000 µm, or about 20 µm to about 1000 µm, or about 50 µm to about 1000 µm, or about 50 µm to about 800 µm, or about 100 µm to about 700 µm. However, in some cases, the capsules can have a diameter up to 2000 µm or 3000 µm if desired, particularly when a larger sample volume may be required.

The capsules, both CTC capsules and CTC-free capsules, are incubated 60 to enable the encapsulated cells to live and grow (FIG. 1). Nutrients in the core can support CTC activity and growth. For the CTC capsules, the activity and growth of the encapsulated CTCs will alter one or more properties of the environment in the core of the CTC capsules to create a simulated tumor microenvironment. Thus, the environment in the core of CTC capsules will typically have a lower pH, as well as other differences, as discussed above, due to cellular activity and growth of the CTCs. On the other hand, the CTC-free capsules will not create a simulated tumor microenvironment.

The incubation 60 of the capsules is carried out in a manner similar to culturing of isolated cells, as described herein and as generally known in the art. Accordingly, incubating 60 the capsules (both CTC capsules and CTC-free capsules) may be for a period of at least about 3 hours, more preferably from about 12 to about 36 hours, or about 18 to about 24 hours. Preferably the capsules are incubated 60 in a medium containing at least one of, or a combination of, the following: an antibiotic, an antioxidant, an anticytokine, and an antiendotoxin.

In some embodiments, the capsules are spread on a supporting surface for the incubation period. Alternatively, the incubated capsules may be spread on the supporting surface. The supporting surface may be made from nitrocellulose, cellulose, dextran, nylon, metal, plastic, latex, agarose, glass, alginate, or a silicon material. The surface is either solid or semisolid. In some embodiments, the glass or plastic surface may be coated with collagen.

The incubated capsules are then contacted 70 with the CAB, which is optionally conjugated with a detectable label (FIG. 1). Because the CTC capsules, after incubation 60, have an internal environment that simulates at least one condition of the tumor microenvironment, the CAB can be preferentially triggered by the internal capsule environment to bind to the cell surface protein on CTCs in the CTC capsules. In the CTC-free capsules the CAB will have a significantly lower binding affinity to the same cell surface protein due to the absence of the trigger condition in the internal capsule environment. With the conjugated detectable label, the CABs bound to CTCs in the CTC capsules can then be detected.

In some embodiments, the capsules are not spread onto a supporting surface, but are incubated 60 and remain in a suspension. The CAB, which is preferably conjugated with a detectable label, may be added to suspension media of the capsule suspension. Due to the permeability of the capsule shell, CAB may penetrate into the capsules and bind to the cell surface protein on a CTC in the CTC capsules.

The CTCs with bound CAB carrying a conjugated detectable label may be detected using a technique selected from fluorescence microscopy, fluorescence microplate reader, flow cytometry, fluorescence-activated cell sorting, fluorometry, and absorption spectroscopy. Detection may also be by means of an image analysis system utilizing a video camera interfaced to a digitizer or other image acquisition system. Detection may also be by visualization through a filter as under a fluorescence microscope. The microscope may just provide a signal that is visualized by the operator. However, the signal may be recorded on photographic film or using a video analysis system. The signal may also simply be quantified in real-time using either an image analysis system or simply a photometer.

The detection, enumeration and/or characterization of CTCs as provided by the present invention are useful in screening cancer, assessing cancer prognosis and in monitoring therapeutic efficacy for early detection of treatment failure that may lead to disease relapse. In addition, the invention enables the detection of early relapse in presymptomatic patients who have completed a course of therapy. This is possible because the presence of CTCs has been associated and/or correlated with tumor progression and spread, poor response to therapy, relapse of disease, and/or decreased survival over a period of time.

Accordingly, in another embodiment, the invention provides a method for screening or, diagnosing cancer in a subject and/or formulating a prognosis for the subject. The method includes detection of CTCs in a sample obtained 10 from the subject. As such, the methods of the present invention may be used, for example, to evaluate cancer patients and/or screen those at risk for cancer. In any of the methods of screening, diagnosis or prognosis as described herein, either the presence or the absence of CTCs, and/or enumeration and/or characterization of the CTCs may be used to generate a diagnosis or prognosis.

In some embodiments, the detection of CTCs in a sample of a subject may be made over a particular time course at various intervals to assess the subject's progression and pathology. For example, analysis may be performed at regular time intervals such as one day, two days, three days, one week, two weeks, one month, two months, three months, six months, or one year, in order to track level and characterization of CTCs as a function of time. In the case of existing cancer patients, this may be used to provide an indication of the progression of the cancer and to assist medical practitioners in making appropriate therapeutic choices. For example, an increase in the CTCs over time may be an indicator of the progression of cancer. Any decrease in the CTCs over time may be an indicator of disease stabilization, remission and/or a patient's response to therapy. For those without cancer or at risk of cancer, a sudden increase in the number of detected CTCs may provide an early warning that the patient has developed a tumor thus providing an early diagnosis.

Once the presence of CTCs in the sample of a subject is confirmed, subsequent analysis may be performed to characterize the CTCs to determine the origin and/or identity of the CTCs and other information about the cancer. For example, in addition to image analysis and bulk number measurements, PCR techniques may be employed, such as multiplexing with primers specific for particular cancer markers to obtain information such as the type of cancer from which the CTCs originated, metastatic state, and degree of malignancy. PCR primers specific for one or more of the following markers may be used: EGFR, 1-IER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, or Leukocyte Associated Receptor (LAR). Additionally, cell size, DNA or RNA analysis, proteome analysis, or metabolome analysis may be performed as a means of obtaining additional information regarding characterization of the patient's cancer. Some cancer markers, including DNA, RNA and protein cancer markers are listed in Table 1.

TABLE 1

Cancer DNA, RNA and Protein Markers

| Cancer type | DNA marker | RNA marker | Protein marker |
|---|---|---|---|
| Head and neck | TP53, microsatellite alterations, presence of HPV and EBV DNA | Cytokeratins | SCC, CD44, CYFRA, telomerase |
| Lung | RAS and TP53 mutations, microsatellite alterations | Cytokeratins, MAGE genes, CEA | CEA, CA125, telomerase, CYFRA |
| Breast | Microsatellite alterations | Cytokeratins, hMAM, MAGE genes, CEA | CA15-3 (MS-1) CEA, CA125 |
| Colon | RAS, APC and TP53 mutations | Cytokeratins, CEA | CEA, CA19-9, CA15-3, telomerase |
| Pancreas | RAS and TP53 mutations | Cytokeratins, CEA | CA19-9 |
| Bladder | TP53 mutations, microsatellite alterations | Cytokeratins, survivin, uroplakin | CEA, CA125, CA19-9, telomerase, survivin, CD44 |
| Prostate | | PSA, MAGE genes, kallikrein | PSA, free PSA, telomerase, kallikrein |

In some embodiments, CTC characterization may include using antibodies targeting protein cancer markers for specific cancer types, especially cancer marker on the CTC surface. The protein cancer markers in Table 1 may be used to determine the cancer types of certain CTCs. For example, CTCs originating from breast cancer typically have surface markers as CK+/DAPI+/CD45-, while CTCs originated from pancreatic cancer typically have surface markers including CA19-9+/EpCAM+. Other cancer markers include breast cancer markers: MUC-1, estrogen, progesterone receptor, cathepsin D, p53, urokinase type plasminogen activator, epidermal growth factor, epidermal growth factor receptor, BRCA1, BRCA2, CA27.29, CA15.5, prostate specific antigen, plasminogen activator inhibitor and Her2-neu; prostate cancer markers: prostate specific antigen, prostatic acid phosphatase, thymosin b-15, p53, HPC1 basic prostate gene, creatine kinase and prostate specific membrane antigen; colon cancer markers: carcinoembryonic antigen, C protein, APC gene, p53 and matrix metalloproteinase (MMP-9); and bladder cancer markers: nuclear matrix protein (NMP22), Bard Bladder tumor antigen (BTA), and fibrin degradation product (FDP).

Therefore, the present invention also provides a method for diagnosing cancer by further characterizing the CTCs in a sample obtained from a subject. Using this method of the invention, a variety of cancers can be detected and diagnosed including, but not limited to, prostate, bladder, renal, lung, ovarian, breast, pancreatic, throat, uterine, brain, blood or testicular cancer. For example, CTCs from prostate, bladder and renal cancer can be detected in urine samples, whereas breast, lung and ovarian cancers can be detected in blood samples.

The following examples are illustrative, but not limiting, of the soft gelatin capsules of the present disclosure. Other suitable modifications and adaptations of the variety of conditions and parameters normally encountered in the field, and which are obvious to those skilled in the art, are within the scope of the disclosure.

EXAMPLES

Example 1: CAB to Axl

Axl is a transmembrane tyrosine kinase with an extracellular domain accessible by the CAB. This cell surface protein is highly expressed in thyroid carcinoma tissues, and overexpressed in many other cancers such as myeloproliferative disorders, prostatic carcinoma cells, or breast cancer. A CAB to the extracellular domain of the Axl protein was developed for the purpose of detecting CTCs.

Figure 2:
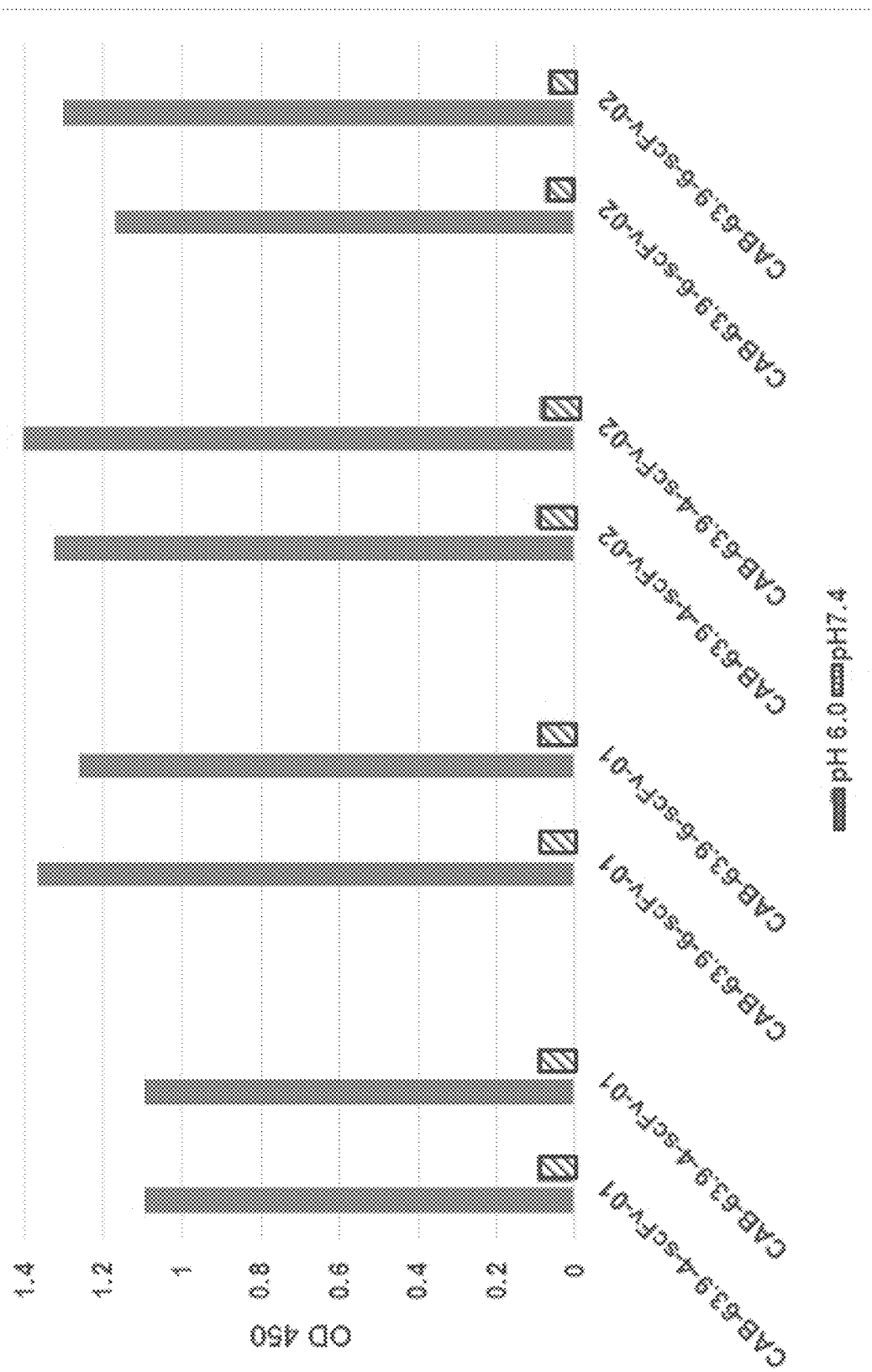
FIG. 2 shows conditionally active antibodies to the extracellular domain of Axl. The conditionally active antibodies were more active at pH 6.0 than at pH 7.4.
Figure 3:
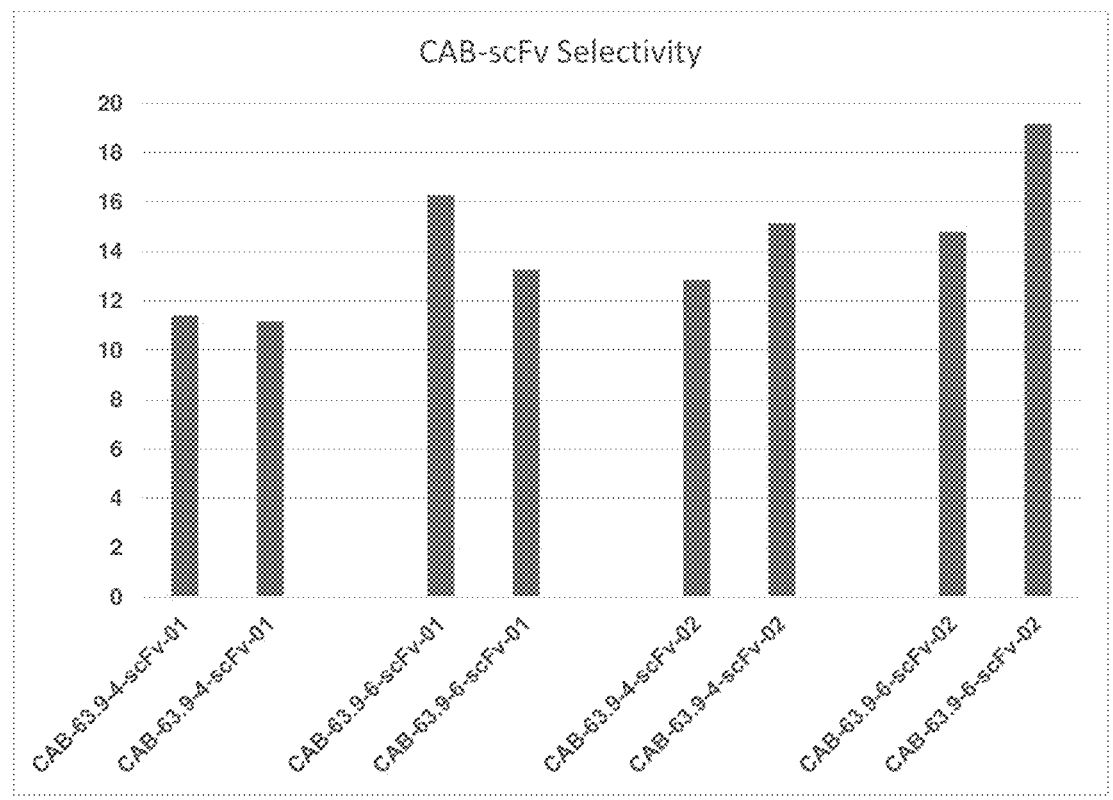
FIG. 3 shows the selectivity of the conditionally active antibodies to the extracellular domain of Axl. The selectivity is measured as a ratio of binding affinity to a target at pH 6.0 to the binding affinity to the same target at pH 7.4.

A wild-type antibody to Axl was selected as the template antibody. The DNA encoding the wild-type antibody was evolved to generate a mutant antibody library. The mutant antibodies in the library were generated by simultaneously screening for selective binding affinity to Axl at pH 6.0 and at pH 7.4. Simultaneously, the expression level of the mutant antibodies were also optimized for the purpose of providing higher yields in a manufacturing process. The screening was done in serum using a FLAG tag because there were human antibodies in the serum which might cause false positives for the screening. The screening buffer was a carbonate buffer (Krebs buffer with ringer—standard buffer but different from PBS). The generated conditionally active antibodies were found to have a higher binding affinity to the Axl at pH 6.0 than the binding affinity to the Axl at pH 7.4, both in comparison with the wild-type antibody. Some of the selected mutant antibodies (scFv) were represented in FIG. 2 with their higher activity at pH 6.0 than at pH 7.4, while their activity ratios of activity at pH 6.0 to pH 7.4 were at least 11 fold (FIG. 3).

Further, these conditionally active antibodies all have high expression levels as shown in Table 2 below, in the column "Clone" showing the antibodies and the expression level "mg/ml" being shown in the second column.

The clones of these antibodies were sent to a service provider with a requested expression level ("amount ordered", expected expression levels). The actual expression levels of these antibodies ("amount delivered") were very high and exceeded the expected expression levels.

TABLE 2

Conditionally active antibodies with high expression levels

| Clone | mg/ml | amount ordered | amount delivered |
|---|---|---|---|
| BAP063.6-hum10F10-FLAG | 7 | 150 | 294 |
| BAP063.6-HC-H100Y-FLAG | 6.6 | 150 | 238 |
| BAP063.8-LC046HC04-FLAG | 7 | 200 | 332.5 |
| BAP063.8-LC062HC02-FLAG | 5.8 | 200 | 220.4 |
| BAP063.9-13-1-FlAG | 5.3 | 50 | 123 |
| BAP063.9-29-2-FLAG | 4.9 | 50 | 102 |
| BAP063.9-45-2-FLAG | 5.4 | 50 | 129 |
| BAP063.9-13-3-FLAG | 5.9 | 50 | 130 |
| BAP063.9-21-3-FLAG | 5.3 | 50 | 117 |
| BAP063.9-21-4-FLAG | 7 | 50 | 176 |
| BAP063.9-29-4-FLAG | 8.2 | 50 | 196 |
| BAP063.9-48-3-FLAG | 7 | 50 | 125 |
| BAP063.9-49-4-FLAG | 5.3 | 50 | 126 |
| BAP063.9-61-1-FLAG | 5.1 | 50 | 97 |
| BAP063.9-61-2-FLAG | 5 | 50 | 92 |

Figure 4:
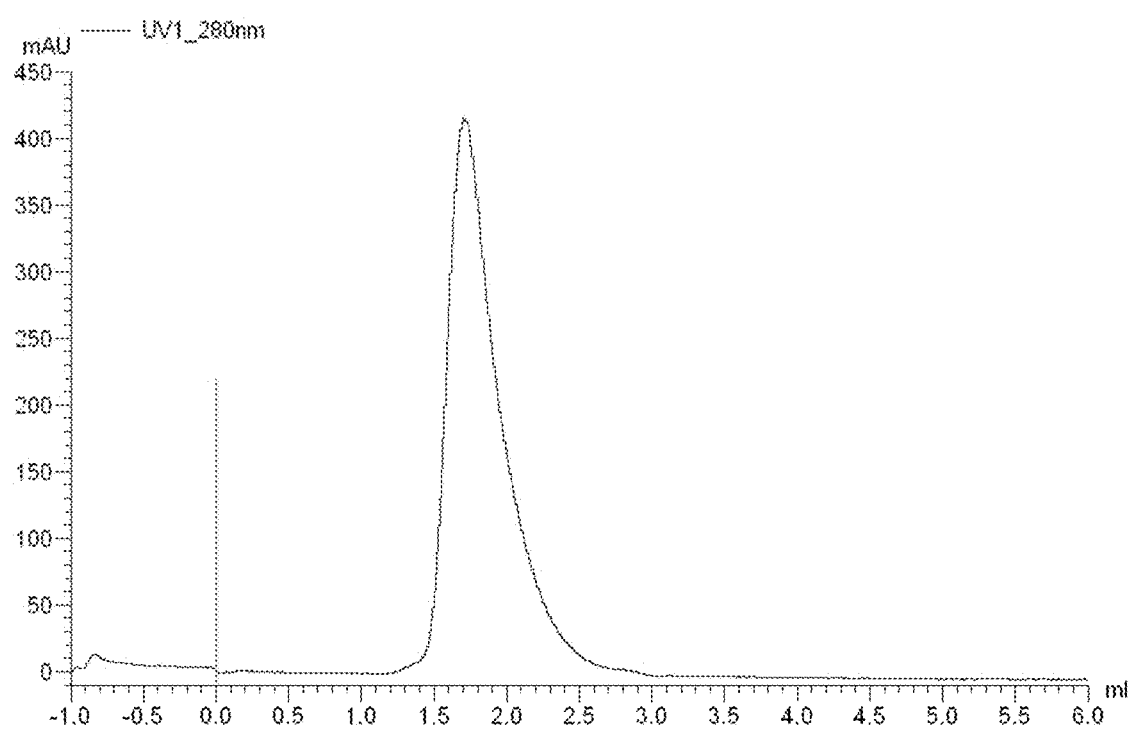
FIG. 4 is a size exclusion chromatograph indicating that the conditionally active antibodies do not aggregate, as described in Example 1.

The conditionally active antibodies did not show aggregation in a buffer as demonstrated in FIG. 4, using BAP063.9-13-1 antibody as an example. The BAP063.9-13-1 antibody was analyzed by size exclusion chromatography. In FIG. 4, only one peak was detected, demonstrating little or no aggregation of the antibody.

The conditionally active antibodies were also assayed using surface plasmon resonance (SPR) to measure their on and off rates to the Axl. The SPR assay has been known to measure on and off rates for the conditionally active antibodies. The SPR assay was performed in the presence of bicarbonate. The in vivo on and off rate (in animals and humans) of the conditionally active antibodies is an important feature for activity and/or selectivity of the conditionally active antibodies.

Figure 5:
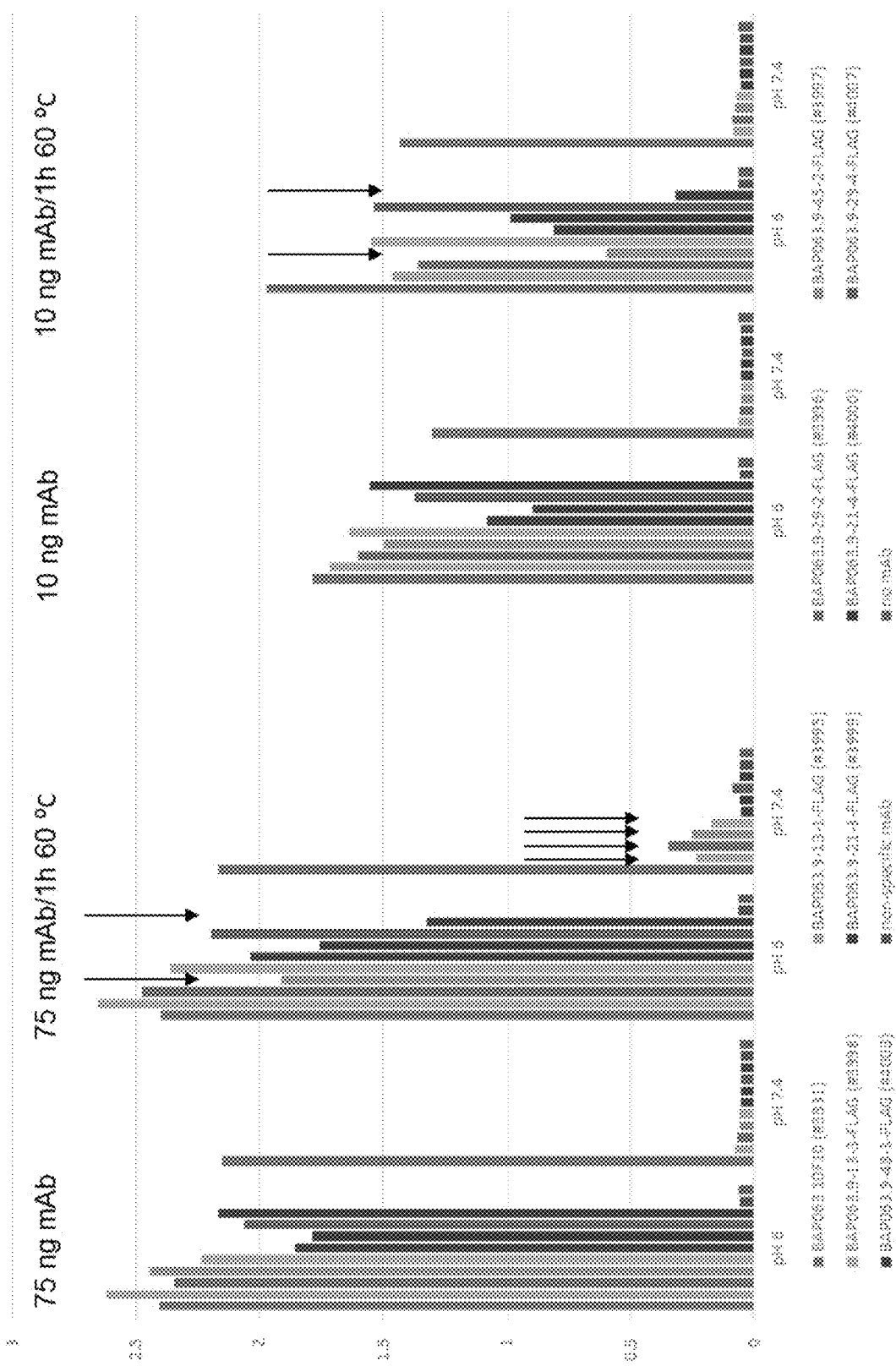
FIG. 5 shows on and off rates of the conditionally active antibodies as measured by a surface plasmon resonance (SPR) assay, as described in Example 1.
Figure 6A:
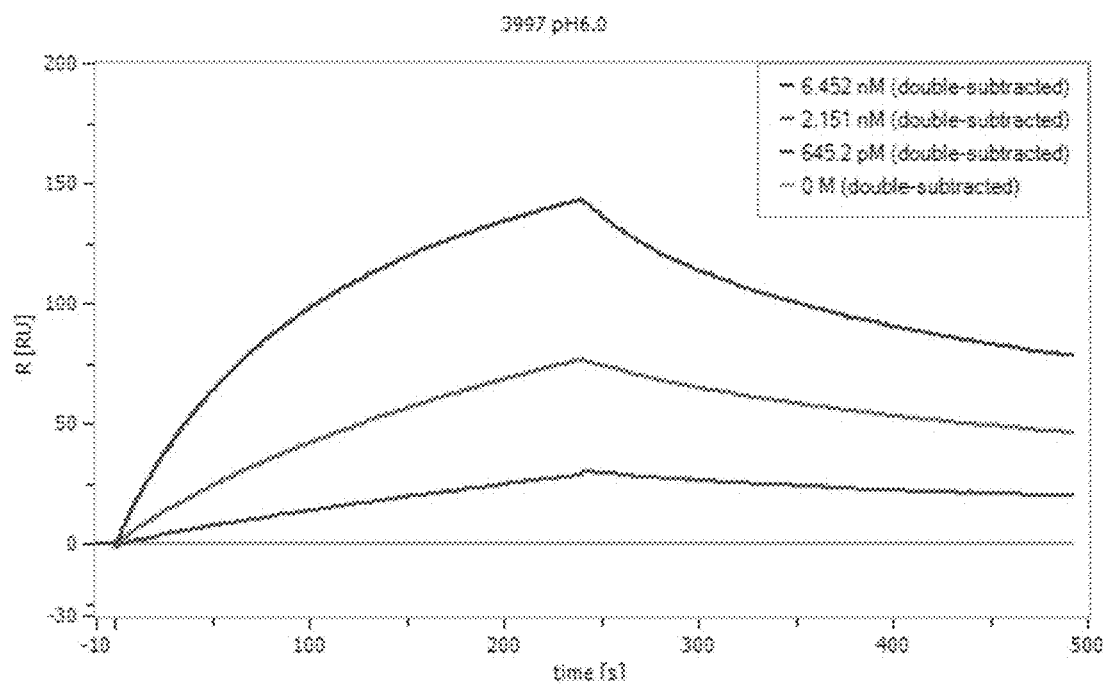
FIGS. 6A and 6B each show the selectivity of the conditionally active antibodies as measured by a SPR assay in Example 1.
Figure 6B:
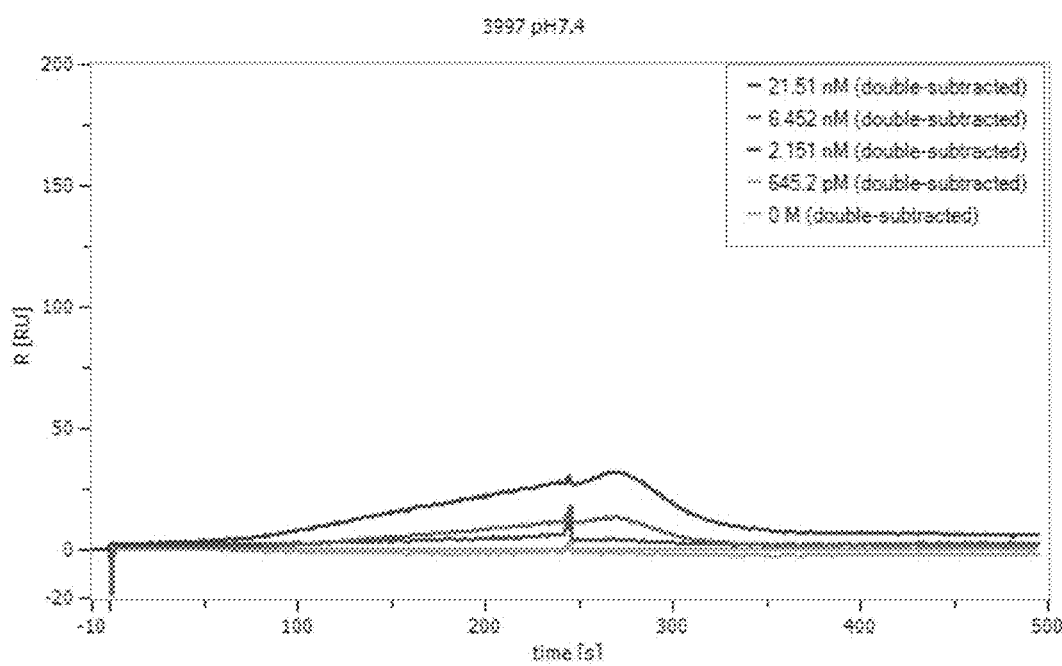

It was observed that the conditionally active antibodies have quick on-rates at pH 6.0 and slower on-rates at pH 7.4, in comparison with the negative control (BAP063 10F10 which has similar on-rates at both pH 6.0 and pH 7.4) (FIG. 5). In addition, raising the temperature from room temperature to 60° C. does not significantly alter the SPR assay results (FIG. 5). The SPR assay also showed that these conditionally active antibodies were highly selective at pH 6.0 as compared to pH 7.4 (FIGS. 6A-6B show one antibody as an example).

The conditionally active antibodies are summarized in Table 3. Two of the antibodies were expressed as scFv (BAP063.9-13.3 and BAP063.9-48.3), which were ready to be inserted into a chimeric antigen receptor (CAR) in the t-cell including the CAR (CAR-T) platform. Incubating the antibodies at 60° C. for one hour did not change the affinities of most of the antibodies ("Thermostability"). In the two columns reporting data using SPR to measure binding affinity at pH 6.0 and pH 7.4 (the last two columns of Table 3), a comparison was made to "BAP063.6-hum10F10-FLAG" (a negative control, second row in Table 3). The selectivity of these antibodies may be determined by the differences between the data in the two last columns. The two scFv antibodies had very high selectivity (75% and 50% at pH 6 over 0% at pH 7.4).

The CAB may be used to detect Axl protein on the surface of CTCs according to the present invention. Similar procedures can be used to make other CABs that are directed to other cell surface proteins and/or that are triggered by a different condition than pH.

TABLE 3

Summary of the conditionally active antibodies

| Clone | CAB scFv | mg/ml | Aggregation (PBS, pH 7.4) | Thermo-stability (1 h 60° C.) | Increased binding at pH 7.4 after heat treatment | Ka(M · s) | Kd[s$^{-1}$] | KD[M] pH 6.0 | SPR activity pH 6.0 | SPR activity pH 7.4 |
|---|---|---|---|---|---|---|---|---|---|---|
| BAP063.6-hum10F10-FLAG | | 7 | No | 100% | No | 5.14E+06 | 8.38E−04 | 1.63E−10 | 100% | 100% |
| BAP063.6-HC-H100Y-FLAG | | 6.6 | N.D. | | | 2.41E+06 | 5.12E−03 | 2.12E−09 | 80% | 40% |

TABLE 3-continued

Summary of the conditionally active antibodies

| Clone | CAB scFv | mg/ml | Aggregation (PBS, pH 7.4) | Thermo-stability (1 h 60° C.) | Increased binding at pH 7.4 after heat treatment | Ka(M · s] | Kd[s$^{-1}$] | KD[M] pH 6.0 | SPR activity pH 6.0 | SPR activity pH 7.4 |
|---|---|---|---|---|---|---|---|---|---|---|
| BAP063.9-13-1-FLAG | | 5.3 | No | 100% | Yes | 1.98E+06 | 2.88E−03 | 1.46E−09 | 100% | 75% |
| BAP063.9-29-2-FLAG | | 4.9 | No | 100% | Yes | 1.19E+06 | 2.14E−03 | 1.79E−09 | 90% | 50% |
| BAP063.9-45-2-FLAG | | 5.4 | No | reduced | Yes | 1.53E+06 | 2.31E−03 | 1.51E−09 | 75% | 25% |
| BAP063.9-13-3-FLAG | Yes | 5.9 | No | 100% | Yes | 1.42E+06 | 1.82E−03 | 1.28E−09 | 75% | 0% |
| BAP063.9-21-3-FLAG | | 5.3 | No | 100% | No | 1.53E+06 | 4.13E−03 | 2.69E−09 | 50% | 25% |
| BAP063.9-21-4-FLAG | | 7 | No | 100% | No | 1.03E+06 | 3.26E−03 | 3.16E−09 | 50% | 0% |
| BAP063.9-29-4-FLAG | | 8.2 | No | 100% | (yes) | 1.40E+06 | 2.21E−03 | 1.58E−09 | 75% | 0% |
| BAP063.9-48-3-FLAG | Yes | 7 | <5% | reduced | No | 8.92E+05 | 2.33E−03 | 2.61E−09 | 50% | 0% |

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

All documents mentioned herein are hereby incorporated by reference in their entirety or alternatively to provide the disclosure for which they were specifically relied upon. The applicant(s) do not intend to dedicate any disclosed embodiments to the public, and to the extent any disclosed modifications or alterations may not literally fall within the scope of the claims, they are considered to be part hereof under the doctrine of equivalents.

What is claimed is:

1. A method of detecting a presence of tumor cells having a cell surface protein in a sample containing cells, said method comprising steps of:
   encapsulating the sample to produce one or more capsules with the sample encapsulated therein wherein the one or more capsules comprise a protein and a nutrient suitable for supporting cell activity and growth of the tumor cells;
   incubating the one or more capsules with the sample encapsulated therein under cell culture conditions suitable for supporting cell activity and growth of the tumor cells whereby the one or more incubated capsules containing said tumor cells produce a first value of a condition of a tumor microenvironment selected from the group consisting of a pH in a range of 6.0-6.8, a partial oxygen pressure in a range of from about 1 to about 20 mmHg and a glucose concentration in a range of from about 0.05 to about 0.5 mM in said capsules containing said tumor cells;
   contacting the encapsulated sample in the one or more incubated capsules with a conditionally active antibody that has a detectably higher binding affinity to the cell surface protein under the first value of the condition of the tumor microenvironment selected from the group consisting of a pH in a range of 6.0-6.8, a partial oxygen pressure in a range of from about 1 to about 20 mmHg and a glucose concentration in a range of from about 0.05 to about 0.5 mM, in comparison with a binding affinity of the conditionally active antibody to the same cell surface protein under a second value of the condition selected from the group consisting of a pH in a range of 7.0-7.8, a partial oxygen pressure in a range of from about 30 to about 50 mmHg, and a glucose concentration in a range of from about 2.5 to about 10 mM; and
   detecting the presence of tumor cells by detecting the detectably higher binding affinity of the conditionally active antibody to the cell surface protein at the first value of the condition of the tumor microenvironment selected from the group consisting of a pH in a range of 6.0-6.8, a partial oxygen pressure in a range of from about 1 to about 20 mmHg and a glucose concentration in a range of from about 0.05 to about 0.5 mM relative to binding affinity of the conditionally active antibody to the cell surface protein under the second value of the condition selected from the group consisting of a pH in a range of 7.0-7.8, a partial oxygen pressure in a range of from about 30 to about 50 mmHg, And a glucose concentration in a range of from about 2.5 to about 10 mM.

2. The method of claim 1, wherein the one or more capsules comprise:
   a core comprising the sample with the cells suspended therein; and
   a shell comprising a biocompatible polymer.

3. The method of claim 2, wherein the core comprises a polymer matrix.

4. The method of claim 2, wherein the biocompatible polymer is selected from the group consisting of proteins and polysaccharides.

5. The method of claim 4, wherein the proteins are selected from the group consisting of albumin, collagen, synthetic polyamino acids and prolamins.

6. The method of claim 4, wherein the polysaccharides are selected from the group consisting of alginate, cellulose and heparin.

7. The method of claim 2, wherein the biocompatible polymer is selected from the group consisting of poly(lactide), poly(glycolide), poly(lactide-co-glycolide), poly(caprolactone), polycarbonates, polyamides, polyanhydrides, polyphosphazene, polyamino acids, polyortho esters, polyacetals, polycyanoacrylates, biodegradable polyurethanes, polyacrylates, ethylene-vinyl acetate polymers, acyl-substituted cellulose acetates, polyurethanes, polystyrenes, polyvinyl chloride, polyvinyl fluoride, poly(vinyl imidazole), chlorosulphonated polyolefins, and polyethylene oxide.

8. The method of claim 2, wherein the core comprises the protein and the nutrient suitable for supporting cell activity and growth of the tumor cells.

9. The method of claim 1, wherein the one or more capsules have a mean diameter of from about 10 μm to about 1000 μm.

10. The method of claim 1, wherein the incubating step is carried out for a period of at least about 3 hours to about 36 hours.

11. The method of claim 1, wherein the conditionally active antibody is conjugated to a detectable label.

12. The method of claim 11, wherein the detectable label is a molecule or an ion directly or indirectly detectable based on light absorbance, fluorescence, reflectance, light scatter, phosphorescence, luminescence properties, radioactive properties, nuclear magnetic resonance properties or paramagnetic properties.

13. The method of claim 1, wherein the cell surface protein is a protein product of a housekeeping gene.

14. The method of claim 13, wherein the housekeeping gene is selected from the group consisting of AP2S1, CD81, GPAA1, LGALS9, MGAT2, MGAT4B, VAMP3, SLC2A1, SLC2A2, SLC2A3, SLC2A4, SLC2A5, SLC2A6, SLC2A7, SLC2A8, SLC2A9, SLC2A10, SLC2A11, SLC2A12, SLC2A13, and SLC2A14.

15. The method of claim 1, wherein the cell surface protein is selected from the group consisting of ABCA7, ABCC1, ABCC5, ABHD3, ACKR3, ADAM10, AQP1, AQP3, ATP13A3, ATP1B3, ATP2B1, ATP2B4, ATP6AP1, ATP6V0A2, BACE1, BMPR2, BNIP2, BST2, BTN2A1, BTN3A3, C12orf76, C17orf62, C1orf27, CCDC107, CD4, CD44, CD46, CD81, CD9, CD99L2, CDAN1, CDIPT, CLCN6, CNNM4, CYP20A1, DCBLD2, DHRS7B, ERBB2, ETNK1, FAM210B, GINM1, GPI, GRAMD1A, HELZ, HERPUD1, HMOX1, HPS3, ICAM1, IFI30, IFRD1, IL15RA, IL6ST, ITGA7, ITGB1, ITGB4, ITGB5, ITSN1, JAG1, LAIR1, LMTK2, LRBA, LRP12, LSR, MACF1, MADD, MCAM, MCOLN1, MET, MICAL3, MPV17L2, NCKIPSD, NDC1, NEO1, NOTCH2, PANX1, PDLIM5, PFDN1, PGAP3, PGRMC2, PHLDB2, PIGN, PIGQ, PIGW, PKN2, PTPRS, PVR, RALGAPA2, RNF145, RNF149, SC5D, SCAMP4, SDC2, SDC4, SLC12A2, SLC16A1, SLC16A3, SLC17A5, SLC19A1, SLC1A5, SLC30A1, SLC38A6, SLC38A7, SLC39A14, SLC3A2, SLC43A1, SLC46A1, SLC46A3, SLC4A2, SLC4A7, SLC7A5, SLC9A1, SMAGP, SORT1, SPG11, SPINT2, SPPL2B, SPPL3, SRD5A3, SRPRB, STX18, STX4, SYVN1, TAPT1, TAZ, TBC1D5, TGFBR2, TM2D2, TMEM183A, TMEM205, TMEM218, TMEM222, TMEM245, TMEM258, TMEM50A, TMEM63B, TMEM97, TNFRSF12A, TXNDC11, UBR2, UQCC1, VSIG4, WWP1, YIPF4, ZDHHC20 and ZDHHC5.

16. The method of claim 1, further comprising a step of expanding a population of the cells in the sample.

17. The method of claim 1, further comprising a step of enriching a population of the cells in the sample.

18. The method of claim 1, wherein the binding affinity of said conditionally active antibody at the first value of the condition in the tumor microenvironment is at least 5 fold higher than the binding affinity of the conditionally active antibody at the second value of the condition.

\* \* \* \* \*

UNITED STATES PATENT AND TRADEMARK OFFICE
CERTIFICATE OF CORRECTION

PATENT NO. : 10,697,972 B2
APPLICATION NO. : 15/404060
DATED : June 30, 2020
INVENTOR(S) : Short Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 130 days.

Signed and Sealed this
Fourteenth Day of February, 2023

Katherine Kelly Vidal
*Director of the United States Patent and Trademark Office*